(12) United States Patent
Beedall et al.

(10) Patent No.: US 9,364,243 B2
(45) Date of Patent: Jun. 14, 2016

(54) ANGULAR ADJUSTMENT MECHANISM, SURGICAL ALIGNMENT GUIDE AND SURGICAL INSTRUMENT ASSEMBLY

(75) Inventors: Duncan Beedall, Leeds (GB); Kevin Booth, Leeds (GB); Gary Fenton, Huddersfield (GB); Alberto Verteramo, Leeds (GB)

(73) Assignee: DEPUY (IRELAND), Cork (IE)

( * ) Notice: Subject to any disclaimer, the term of this patent is extended or adjusted under 35 U.S.C. 154(b) by 390 days.

(21) Appl. No.: 13/885,236

(22) PCT Filed: Nov. 8, 2011

(86) PCT No.: PCT/GB2011/052173
§ 371 (c)(1),
(2), (4) Date: Sep. 5, 2013

(87) PCT Pub. No.: WO2012/066306
PCT Pub. Date: May 24, 2012

(65) Prior Publication Data
US 2013/0338671 A1  Dec. 19, 2013

(30) Foreign Application Priority Data
Nov. 18, 2010  (GB) .................................. 1019490.0

(51) Int. Cl.
*A61B 17/15* (2006.01)
*A61B 17/17* (2006.01)
(52) U.S. Cl.
CPC ........... *A61B 17/1764* (2013.01); *A61B 17/155* (2013.01)
(58) Field of Classification Search
CPC ..... A61B 17/15; A61B 17/154; A61B 17/155
See application file for complete search history.

(56) References Cited

U.S. PATENT DOCUMENTS 1,440,072 A   12/1922   Greener
4,453,539 A   6/1984   Raftopoulos
(Continued)

FOREIGN PATENT DOCUMENTS

EP  687448 A1  12/1995
EP  689796 A1  1/1996
(Continued)

OTHER PUBLICATIONS

Labourdette, P.; Femoral-Patellar Prosthesis and Ancillary Device for Making a Trochlear Impression for Receiving Said Prosthesis; European Publication No. EP687448A1; Dec. 20, 1995; English Abstract; MicroPatent Report; 2010 MicroPatent LLC.
(Continued)

*Primary Examiner* — Christian Sevilla
*Assistant Examiner* — Eric S Gibson

(57) ABSTRACT

An angular adjustment mechanism for a surgical instrument is described. The mechanism comprises an adjustment member (102) configured for rotation about a longitudinal axis (122), the adjustment member comprising a plurality of pairs of facets (134) arranged about the longitudinal axis. Each of the plurality of pairs of facets defines a respective angled axis (148B,148C) at an angle (150B,150C) relative to the longitudinal axis. A pivoting member (104) is arranged to pivot about a pivot axis perpendicular to the longitudinal axis and comprises a recess (128) for receiving the adjustment member and engaging one pair of the plurality of pairs of facets. This provides an angular adjustment mechanism in which facets on the outside of the adjustment member engage corresponding surfaces in a recess on a pivoting member. The use of facets provides a secure connection while allowing a greater degree of angular adjustment and providing a further benefit of simple operation.

2 Claims, 22 Drawing Sheets

(56) References Cited

U.S. PATENT DOCUMENTS

| | | | | |
|---|---|---|---|---|
| 4,703,751 A * | 11/1987 | Pohl | .................. | A61B 17/155 606/53 |
| 5,116,335 A | 5/1992 | Hannon | | |
| 5,454,816 A * | 10/1995 | Ashby | .................. | A61B 17/155 606/102 |
| 5,484,446 A * | 1/1996 | Burke | .................. | A61B 17/154 606/86 R |
| 5,562,674 A * | 10/1996 | Stalcup | .................. | A61B 17/155 606/87 |
| 5,628,749 A | 5/1997 | Vendrely | | |
| 5,693,048 A * | 12/1997 | Stalcup | .................. | A61B 17/155 606/86 R |
| 5,830,216 A * | 11/1998 | Insall | .................. | A61B 17/155 606/87 |
| 5,910,143 A * | 6/1999 | Cripe | .................. | A61B 17/155 606/86 R |
| 5,910,173 A * | 6/1999 | DeCarlo, Jr. | .................. | A61F 2/30771 128/898 |
| 6,013,081 A | 1/2000 | Burkinshaw | | |
| 6,077,270 A * | 6/2000 | Katz | .................. | A61B 17/154 606/102 |
| 6,193,723 B1 | 2/2001 | Cripe et al. | | |
| 6,558,391 B2 * | 5/2003 | Axelson, Jr. | .................. | A61B 17/155 606/88 |
| 6,613,052 B1 | 9/2003 | Kinnett | | |
| 6,916,325 B2 * | 7/2005 | Kana | .................. | A61B 19/46 606/89 |
| 6,979,299 B2 * | 12/2005 | Peabody | .................. | A61B 5/1072 33/511 |
| 7,374,563 B2 * | 5/2008 | Roger | .................. | A61B 17/155 606/88 |
| 7,628,793 B2 * | 12/2009 | Calton | .................. | A61B 17/157 606/88 |
| 7,794,467 B2 | 9/2010 | McGinley | | |
| 7,959,637 B2 * | 6/2011 | Fox | .................. | A61B 17/1764 606/87 |
| D651,318 S * | 12/2011 | Cronin | .................. | A61B 17/1764 D24/140 |
| 8,152,807 B2 * | 4/2012 | Edwards | .................. | A61B 17/1725 606/62 |
| 8,287,541 B2 | 10/2012 | Nelson | | |
| 8,979,847 B2 * | 3/2015 | Belcher | .................. | A61B 17/155 606/79 |
| 9,101,443 B2 * | 8/2015 | Bonutti | .................. | A61B 17/025 |
| 2002/0198531 A1 | 12/2002 | Millard | | |
| 2004/0153084 A1 | 8/2004 | Haney | | |
| 2006/0036248 A1 | 2/2006 | Ferrante | | |
| 2008/0097451 A1 | 4/2008 | Chen | | |
| 2008/0177337 A1 * | 7/2008 | McGovern | .................. | A61B 17/155 606/86 R |
| 2009/0043310 A1 * | 2/2009 | Rasmussen | .................. | A61B 17/025 606/88 |
| 2009/0125114 A1 * | 5/2009 | May | .................. | A61B 17/1764 623/20.14 |
| 2009/0149964 A1 * | 6/2009 | May | .................. | A61B 17/155 623/20.15 |
| 2010/0010493 A1 * | 1/2010 | Dower | .................. | A61B 17/157 606/87 |
| 2010/0121334 A1 * | 5/2010 | Couture | .................. | A61B 17/155 606/87 |
| 2010/0234850 A1 * | 9/2010 | Dees, Jr. | .................. | A61B 17/155 606/87 |
| 2010/0292694 A1 * | 11/2010 | Kecman | .................. | A61B 17/155 606/62 |
| 2011/0009868 A1 * | 1/2011 | Sato | .................. | A61B 17/1764 606/87 |
| 2011/0071537 A1 | 3/2011 | Koga | | |
| 2013/0317501 A1 * | 11/2013 | Booth | .................. | A61B 17/72 606/62 |
| 2013/0331844 A1 * | 12/2013 | Booth | .................. | A61B 17/155 606/88 |
| 2013/0338671 A1 * | 12/2013 | Beedall | .................. | A61B 17/1764 606/88 |
| 2014/0324054 A1 * | 10/2014 | Dmuschewsky | .................. | A61B 17/155 606/89 |

FOREIGN PATENT DOCUMENTS

| | | | |
|---|---|---|---|
| EP | 1444957 A1 | 8/2004 | |
| EP | 1574177 A1 | 9/2005 | |
| FR | 2943528 A1 | 10/2010 | |
| WO | WO 9618351 A1 | 6/1996 | |
| WO | WO 02058575 A1 | 8/2002 | |
| WO | WO 2006090361 A2 | 8/2006 | |
| WO | WO 2009006741 A1 | 1/2009 | |
| WO | WO 2009037471 A2 * | 3/2009 | ........... A61B 17/155 |

OTHER PUBLICATIONS

PCT International Search Report and Written Opinion PCT/GB2011/052173 dated Feb. 24, 2012.

GB Search Report 1019490.0 dated Feb. 15, 2011.

Japanese Search Report From Corresponding Japanese Patent Application No. 2013-539338 With a Mail Date of Sep. 1, 2015, 2 Pages.

* cited by examiner

ANGULAR ADJUSTMENT MECHANISM, SURGICAL ALIGNMENT GUIDE AND SURGICAL INSTRUMENT ASSEMBLY

CROSS REFERENCE TO RELATED APPLICATION

This application is a National Stage 35 U.S.C. 371 of International Patent Application PCT/GB2011/052173, filed Nov. 8, 2011.

BACKGROUND OF THE INVENTION

The present invention relates to an angular adjustment mechanism, surgical alignment guide and surgical instrument assembly. The present invention is particularly applied to orthopaedic surgery and especially knee surgery.

In orthopaedic knee surgery, a cut may be made to the femoral head in order to correct varus or valvus alignment. A cutting guide is used to locate the cut accurately. A cutting guide is fixed to the bone using pins and provides a stable surface to guide resection of the femoral head.

In order to ensure the cutting guide is placed correctly on the femur, an alignment system is typically used. An intramedullary rod is inserted into the intermedullary canal of the femur, providing a stable reference to the intramedullary axis of the femur. An alignment guide is disposed on this rod. The alignment guide contains a scale indicating the desired angle of the cut relative to the intramedullary axis of the femur and an angular adjustment mechanism. The cutting guide is attached to the alignment guide and advanced along the rod until it is in contact with the femur. It is aligned at the desired angle by the alignment guide. It can then be secured in place.

WO-A-2009/037471 describes an example of such an alignment guide. The instrument comprises an angular adjustment mechanism which includes an adjustment member which is rotatable about the longitudinal axis of an intramedullary rod. The adjustment member has an end surface defining a plurality of slots located between recesses or notches, giving the end of the adjustment member a castellated appearance. Each slot defines a different angle relative to the longitudinal axis. A selected slot engages a rib formed on a pivoting member, thereby rotating the pivoting member to a desired angle.

The mechanism of WO-A-2009/037471 has disadvantages because the space available for the adjustment member limits its size. The size sets a limit on the number of different slots the adjustment member can define to ensure that the pivoting member is held securely. In practice, the recess needs to be of a minimum width to engage the ridge firmly. The walls defining the recess also need to have a minimum size to prevent their deformation or failure. The limit on the number of slots limits the range of adjustment possible. For example, WO-A-2009/037471 discusses an embodiment in which the angular adjustment is in increments of 2 degrees or greater, for example, different slots define 3, 5 or 7 degrees of angular adjustment. It would be desirable to provide an alignment guide in which the angular adjustment mechanism can provide finer degrees of angular adjustment.

Accordingly, the present invention provides an angular adjustment mechanism in which facets on the outside of the adjustment member engage corresponding surfaces in a recess on a pivoting member. The use of facets allows a secure connection to be achieved without requiring intermediate walls or edges as are required using a slot on the angular adjustment member as taught by WO-A-2009/037471 (because the walls are necessary to define the recess). This allows a greater degree of angular adjustment and a further benefit of simpler operation.

According to a first aspect of the present invention there is provided an angular adjustment mechanism for a surgical instrument comprising an adjustment member configured for rotation about a longitudinal axis, the adjustment member comprising a plurality of pairs of facets arranged about the longitudinal axis; wherein each of the plurality of pairs of facets defines a respective angled axis at an angle relative to the longitudinal axis; and a pivoting member arranged to pivot about a pivot axis perpendicular to the longitudinal axis and comprising a recess for receiving the adjustment member and engaging one pair of the plurality of pairs of facets.

BRIEF SUMMARY OF THE INVENTION

Each pair of facets may be mutually opposed about the longitudinal axis. The plurality of pairs of facets may extend completely around the longitudinal axis or only partially around the longitudinal axis.

The pivot axis preferably intersects the longitudinal axis for simplicity of construction, however, this is not essential and it could be located elsewhere in some embodiments, for example, by using a linkage.

Each of the plurality of pairs of facets may define a respective angled axis which is at a different angle relative to the longitudinal axis than others of the plurality of pairs of facets, although in some embodiments there may be duplication of the angled axis between different pairs of facets, depending on the application.

The adjustment member is preferably translatable along the longitudinal axis to allow it to disengage and engage the recess. However, other arrangements are possible, for example, manufacturing one or both of the facets and/or the recess from a resilient material, enabling deformation to allow rotation of the adjustment member in situ within the recess.

In use, the respective angled axis defined by each pair of facets allows the angle of the pivoting member to be set by rotation of the adjustment member. For example, in one embodiment the facets may be provided with a regular difference between each angled axis, for example each pair of facets may differ from an immediately adjacent pair in one degree steps, two degree steps or any other amount as appropriate. One embodiment comprises an odd number of pairs of facets. This enables one pair to define a zero degree pivot and the other pairs to define the same range of positive and negative (clockwise or anticlockwise) rotation about the pivot axis.

An angular adjustment mechanism according to the invention can provide a finer degree of adjustment than the prior art. This is because the facets engage the recess and they are defined by a surface of the adjustment member itself, no walls are needed as are required when a recess is used. A further benefit of the use of facets is easier cleaning and assembly.

Preferably, each respective angled axis is defined by rotating each of the plurality of pairs of facets about the same predetermined point on the longitudinal axis. This simplifies construction by ensuring that whichever pair of facets is selected, the rotation is about the same point, without a need to provide an intermediate linkage mechanism.

In one embodiment, the pivot axis intersects the longitudinal axis and the predetermined point on the longitudinal axis is where the pivot axis intersects the longitudinal axis. This enables the adjustment member to directly alter the position of the pivoting member without requiring an intermediate linkage.

Each facet of the plurality of pairs of facets may be substantially planar and the axis of rotation for each respective angled axis may then be parallel to the plane of the facets and perpendicular to the longitudinal axis. This means that the axis of rotation is in a slightly different direction for each pair of facets, it is not the same for every pair of facets. The effect is that the axis of rotation rotates around the predetermined point depending on which pair of facets is selected. This rotation ensures that when a selected pair of facets are engaged in the recess the axis of rotation of those facets is aligned with the pivot axis.

Preferably, each of the plurality of pairs of facets define a taper in the direction of the angled axis. The taper means that the facets present a narrowing profile in the direction of the angled axis. This provides a self-centering effect to ensure that the adjustment member is securely located within the recess. It also simplifies engagement and release of the adjustment member as required while still ensuring a secure connection when the adjustment member is engaged in the recess.

Preferably, the taper angle is between ten degrees and thirty degrees. The reference to the taper angle refers to the angle formed between the planes defined by each pair of facets if the planes are extended to the point where the two planes intersect. Preferably the taper angle is greater than the range of angular adjustment between the respective angled axes. This is preferred to ensure that the taper is still present no matter what the rotation of the angular adjustment member. For example, if a degree of angular adjustment of ±9° is required, the total adjustment is 18° and a taper angle of 20° or more is preferred. This ensures that even at the extreme adjustment of ±9° there is still a slight taper at both sides with respect to the longitudinal axis.

In one embodiment, each of the plurality of pairs of facets is contiguous with another of the plurality of pairs of facets. The plurality of pairs of facets then extend all the way around the longitudinal axis.

At least a part of each edge between respective ones of the plurality of facets may then be cut away or scalloped. This cut away will extend partially into the facet itself. The cut away portion enables easier rotation of the angular adjustment member to select an alternative pair of facets. Without the cut away, the edge between facets may snag on the recess. Including the cut away means that a smaller amount of translational movement of the adjustment member along the longitudinal axis is required to disengage a pair of facets from the recess sufficiently to enable rotation to select a different pair of facets.

Preferably, each respective angled axis is defined by rotating each of the plurality of pairs of facets about the same predetermined point on the longitudinal axis and the cut away portion of each edge extends for the same distance from the predetermined point in the direction of the respective angled axis. Thus, when viewed along the longitudinal axis, the cut away portion extends different lengths on each side of the adjustment member, relative to the longitudinal axis. This ensures that sufficient portion is cut away to enable the improved rotation of the adjustment member, but the length of cut away is minimised to improve the surface area of the facet available to engage with the recess.

The recess may comprise a pair of mutually opposed projections for engaging one of the plurality of pairs of facets. Use of a projection has been found to provide a secure connection with the facet while enabling easier adjustment of the angular adjustment member if required. Alternative embodiments may not use a projection and in that case the facet may directly engage a side of the recess.

The angular adjustment mechanism may further comprise a resilient member for biassing the adjustment member into the recess of the pivot member. This helps to ensure a secure connection between the adjustment member and the pivot member.

The angular adjustment mechanism described above may form part of a surgical alignment guide. The surgical alignment guide may be combined with a cutting guide attached to the pivot member to form a surgical instrument assembly. The cutting guide can be directly or indirectly attached to the pivot member. If the cutting guide is indirectly attached to the pivot member and intermediate portion may be connected between the cutting guide and the pivot member.

The surgical instrument assembly may further comprise an intramedullary rod defining an intramedullary axis. In that case the angular adjustment mechanism is installed on the intramedullary rod and the longitudinal axis of the adjustment member is coaxial with the intramedullary axis.

BRIEF DESCRIPTION OF THE DRAWINGS

Embodiments of the invention will now be described by way of example only with reference to the accompanying drawings, in which.

DETAILED DESCRIPTION OF THE INVENTION

Figure 1:
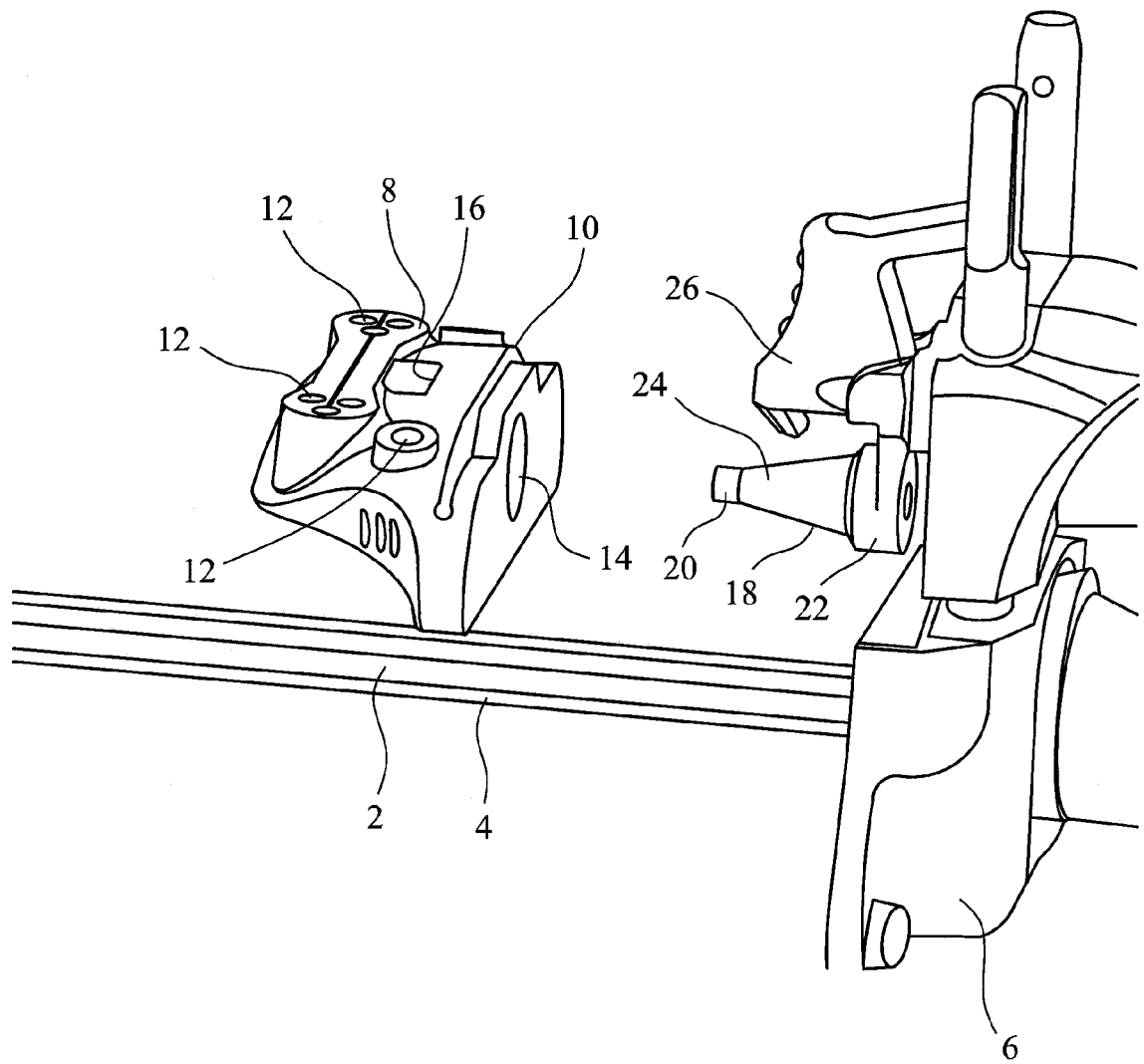
FIG. 1 depicts a perspective view of an alignment guide, cutting guide and intramedullary rod before connection of the cutting guide to the alignment guide.

FIG. 1 depicts a perspective view showing components of a surgical instrument system for aligning a cutting guide. The system comprises an intramedullary rod which comprises a cylindrical member 2 having longitudinal grooves 4 formed along its length. In use the cylindrical section 2 is inserted into the intramedullary canal of a femur and the longitudinal grooves 4 provide means for pressure release during insertion.

An alignment guide 6 (shown partially in FIG. 1) comprises a through bore into which the cylindrical section 2 of the intramedullary rod is inserted, so that the alignment guide 6 can move longitudinally along the cylindrical section 2 and also rotate relative to the cylindrical section.

A cutting guide 8 is provided separately from the alignment guide 6. The cutting guide 8 comprises a cutting slot 10 which defines the cut to be made to the bone. Cutting guide 8 also comprises attachment holes 12 for fixing the cutting guide 8 to the bone. Cutting guide 8 is attached to the alignment guide 6 by means of a recess 14 and an attachment surface 16 on its upper surface. The recess 14 has a shape corresponding to an attachment protrusion 18 formed on the alignment guide 6.

Attachment protrusion 18 comprises a first cylindrical portion 20 having a first diameter and a second cylindrical portion 22 having a second diameter which is larger than the first diameter. The first diameter is about 4 mm and the second diameter is about 12 mm in this embodiment. Other dimensions may be used in other embodiments. The first and second cylindrical portions 20, 22 share a common axis. Joining the first cylindrical section to the second cylindrical section 22 is a generally frustoconical portion 24. The recess 14 defines surfaces corresponding to the first and second cylindrical portions 20, 22 of the attachment protrusion 18.

In use, when the attachment protrusion 18 is inserted into recess 14, first cylindrical portion 20 and second cylindrical portion 22 engage corresponding surfaces within the recess so that the cutting guide 8 is securely aligned with the longitudinal axis of the attachment protrusion 18. The dimensions of the corresponding surfaces within the recess are close to the dimensions of the first cylindrical portion 20 and the second cylindrical portion 22 but very slightly larger. This ensures firm connection but reduces the likelihood of a tight fit between the attachment protrusion 18 and the recess 14 making it difficult to remove the attachment protrusion 18 from the recess 14.

Figure 2:
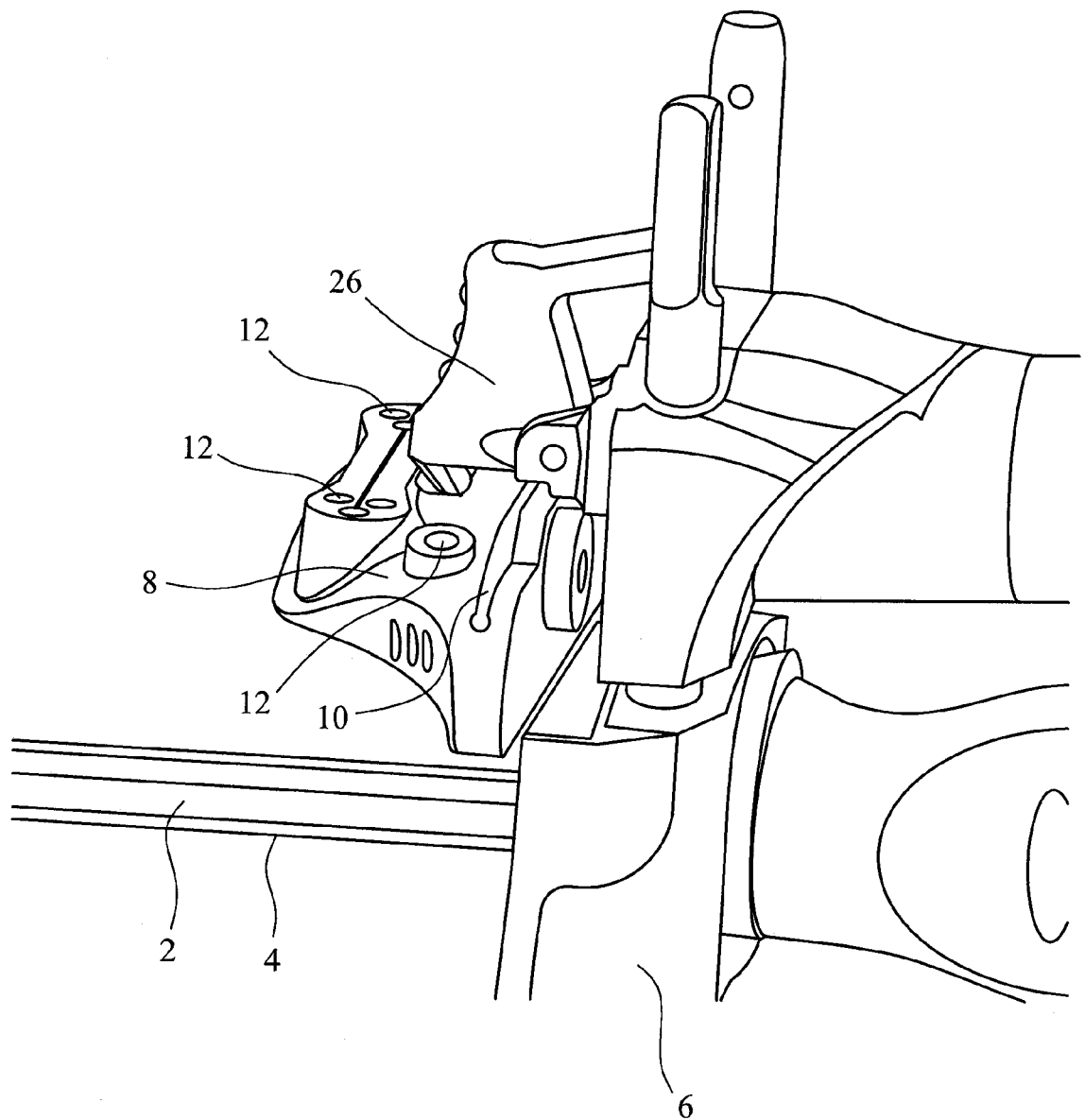
FIG. 2 depicts a perspective view of an alignment guide, cutting guide and intramedullary rod as shown in FIG. 1, after the cutting guide has been connected to the alignment guide.

The cutting guide 8 is further secured in place on the attachment protrusion 18 of the alignment guide 6 by a clip member 26 on the alignment guide 6. The clip member 26 engages the attachment surface 16 of the cutting guide 8. A perspective view of the cutting guide 8 installed on the alignment guide 6 can be seen in FIG. 2.

Figure 3:
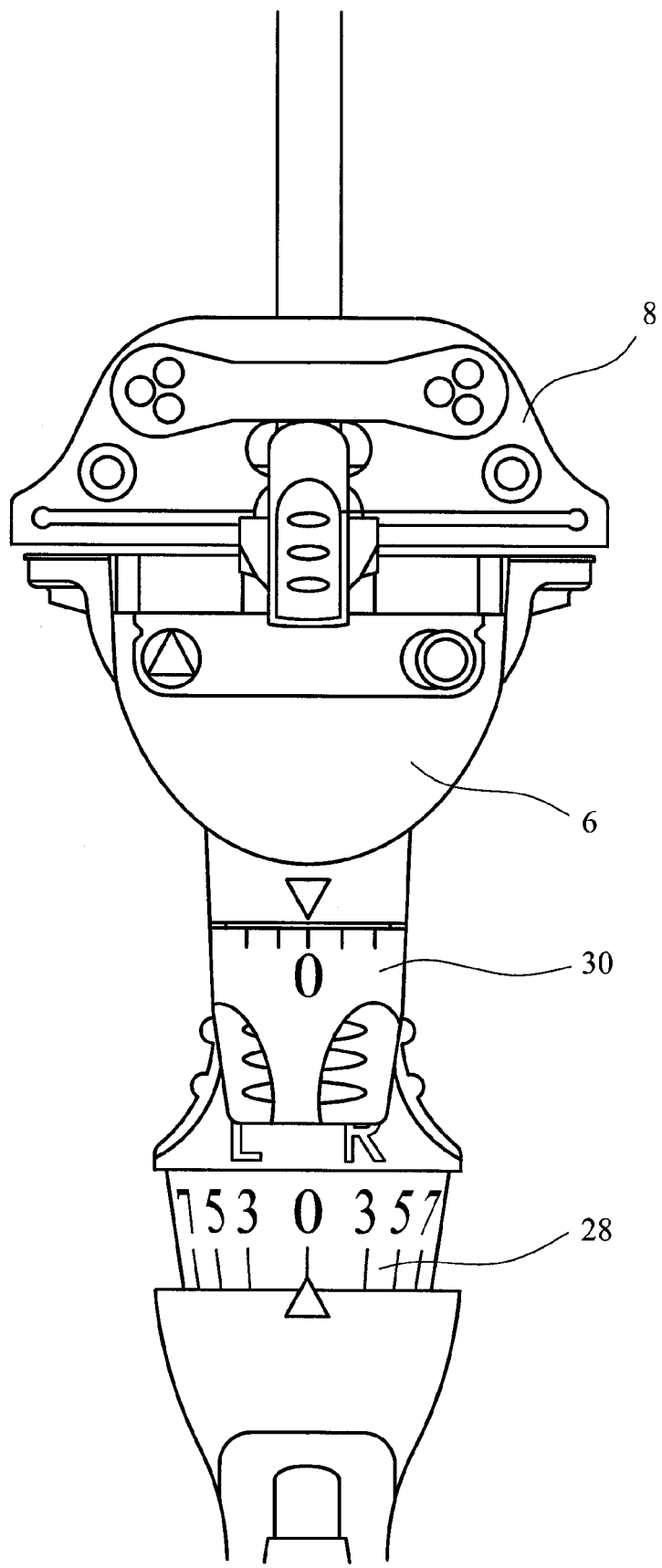
FIG. 3 shows a plan view of the system of alignment guide, cutting guide and rod of FIG. 2.

FIG. 3 shows a plan view of the system of alignment guide 6, cutting guide 8 and rod assembled together. FIG. 3 also depicts two adjustment scales 28, 30 provided on the alignment guide 6. The two adjustment scales 28, 30 allow the relative rotation of parts of the alignment guide to be set as determined by a surgeon to alter the varus valgus rotation of the attachment protrusion 18 relative to the intramedullary axis defined by the cylindrical portion 2 of the rod and the through bore in the alignment guide 6. The cutting guide 8 is installed on the attachment protrusion 18 and hence its alignment is altered relative to the intramedullary axis.

Figure 4:
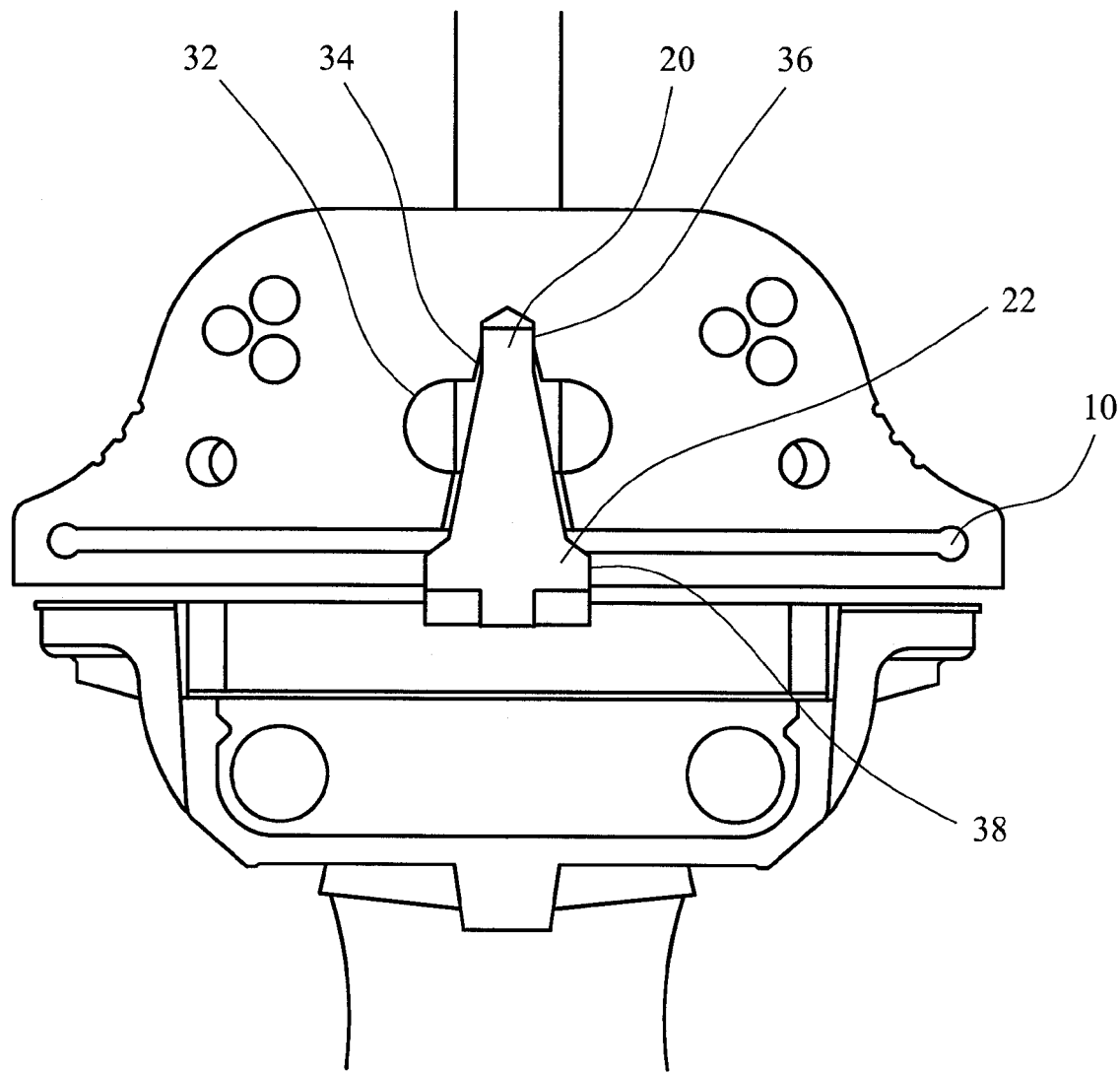
FIG. 4 depicts a cross-section through the attachment protrusion and corresponding recess when the alignment guide has been connected to the cutting guide.

FIG. 4 depicts a cross-section of the assembled system, taken through the connection recess. This shows how the cutting guide is secured on the alignment guide by the engagement of cylindrical portions 20, 22 in corresponding sections of the recess. FIG. 4 also enables the internal construction of the connection recess 14 to be understood more clearly. The cross-section illustrates enlarged portion 32. Enlarged portion 32 includes an initial section perpendicular to the longitudinal axis of the recess following a short tapered section 34 from the first cylindrical section. Enlarged section 32 has a greatest dimension perpendicular to the longitudinal axis which is larger than the diameter of the second cylindrical section. This provides a greater range of movement for the first cylindrical section 20 within the recess during disconnection of the alignment guide 6 from the cutting guide 8. Tapered section 34, adjacent the first cylindrical section 36 of the cutting guide 8 serves to guide the tip of the attachment protrusion 18 into the first cylindrical section 36.

The enlarged central section 32 extends perpendicular to the longitudinal axis through the entire depth of the cutting guide. This allows the enlarged central section to also provide attachment surface 16 for clip 26.

The second cylindrical section is formed in the portion of the cutting guide adjacent cutting slot 10.

Figure 5A:
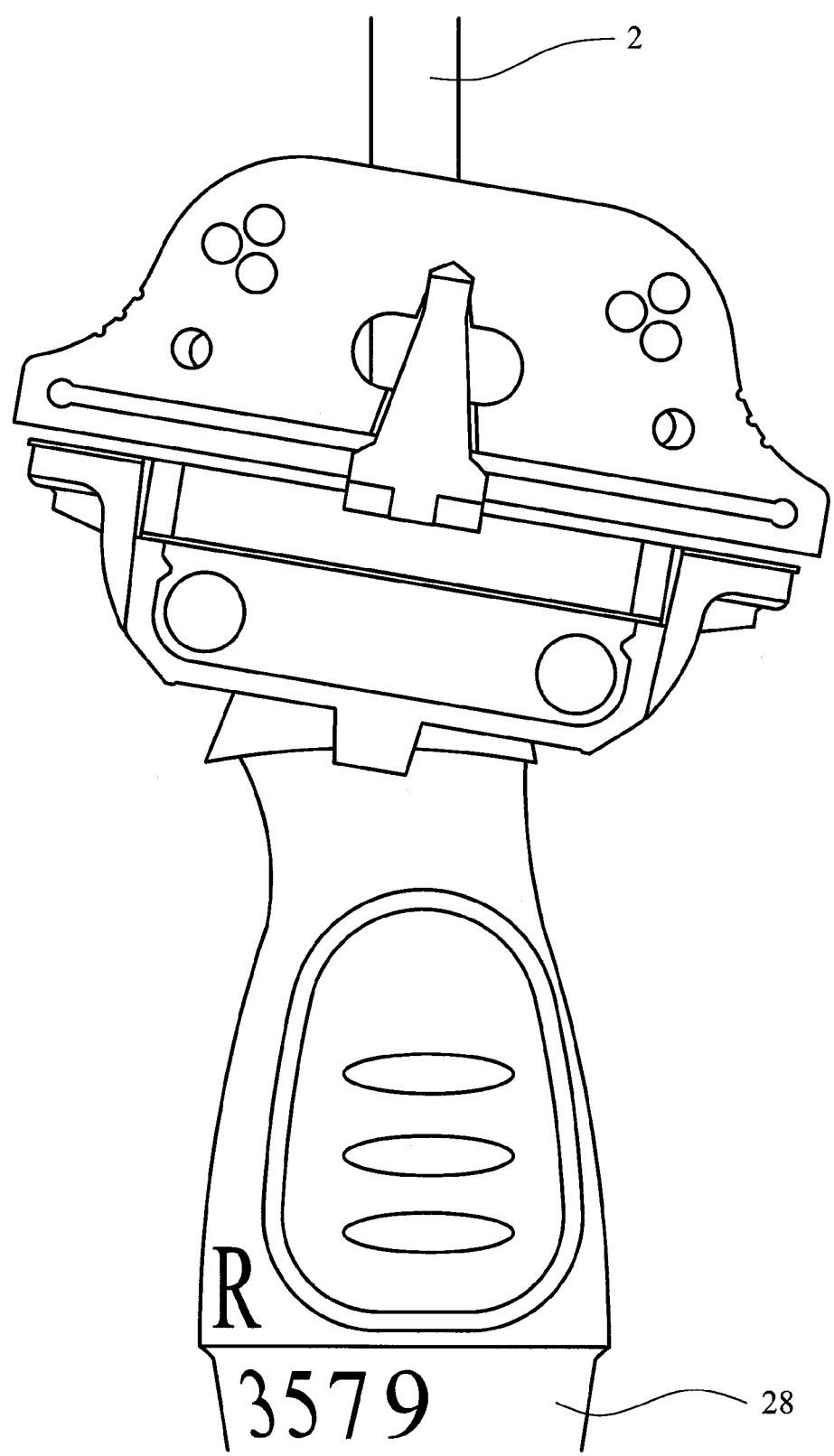
FIGS. 5a-5e show cross-sections through the alignment guide and cutting guide showing the disconnection of the alignment guide from the cutting guide.

The disconnection of the cutting guide from the alignment guide will now be described. To illustrate the benefits of this system, the cutting guide is depicted in FIG. 5a connected to the alignment guide 6 with the varus valgus adjustment 28 of the alignment guide adjusted to a maximum in the right-hand direction. This shifts the angle of the longitudinal axis of the attachment protrusion 18 and cutting guide 8 relative to the longitudinal axis of the cylindrical section 2, and can clearly be seen in FIG. 5a. In prior art devices this configuration can be difficult for a surgeon to disconnect the alignment guide from the cutting guide. The difference in angles between the anatomic axis (defined by the cylindrical section 2 of the rod) and the mechanical axis, in addition to the offset of the attachment protrusion with the alignment guide make it difficult to remove cleanly. The alignment guide is constrained by the cylindrical section 2 to move along the anatomical axis, not mechanical axis.

Figure 5B:
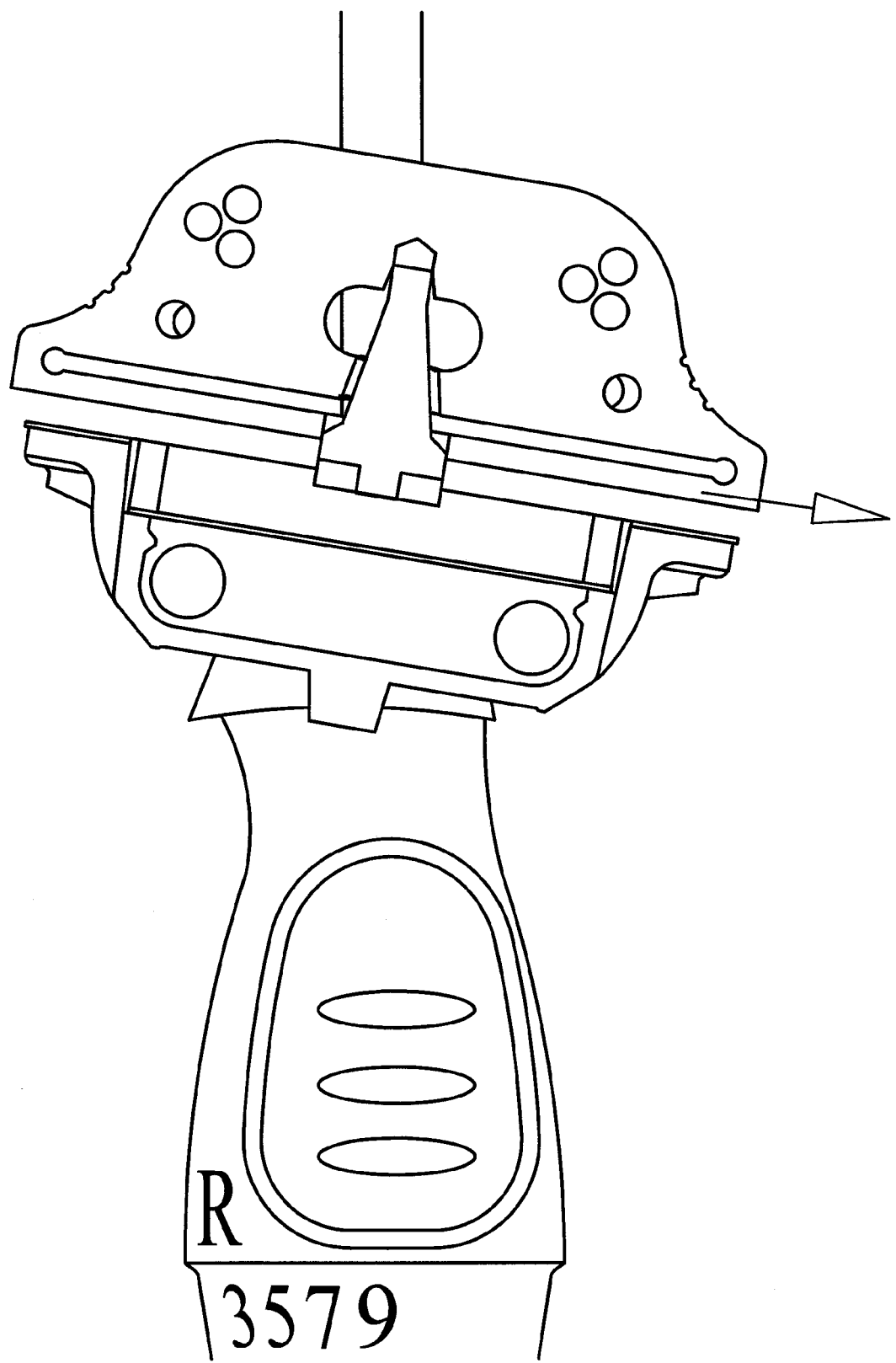
Figure 5C:
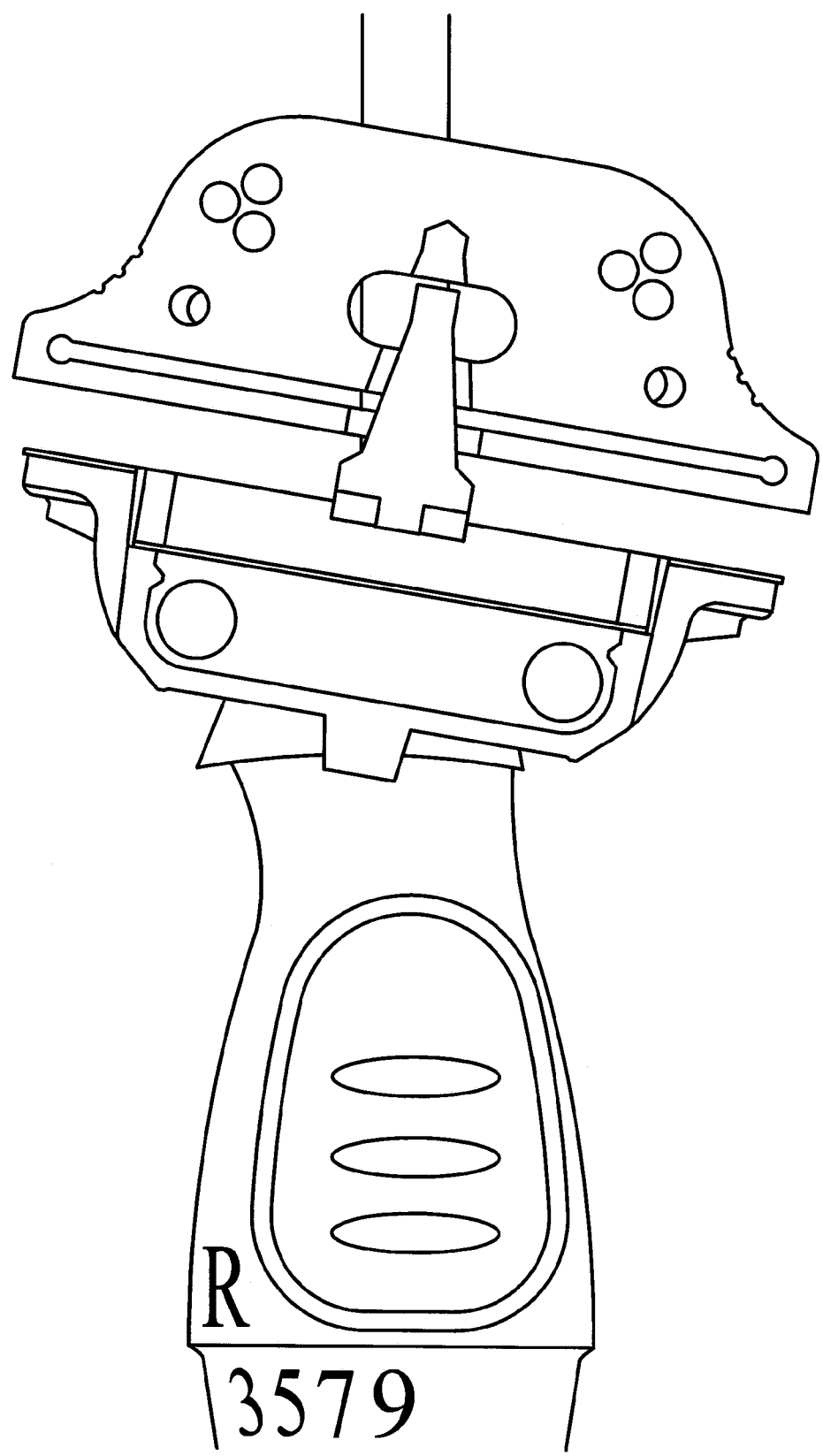
Figure 5D:
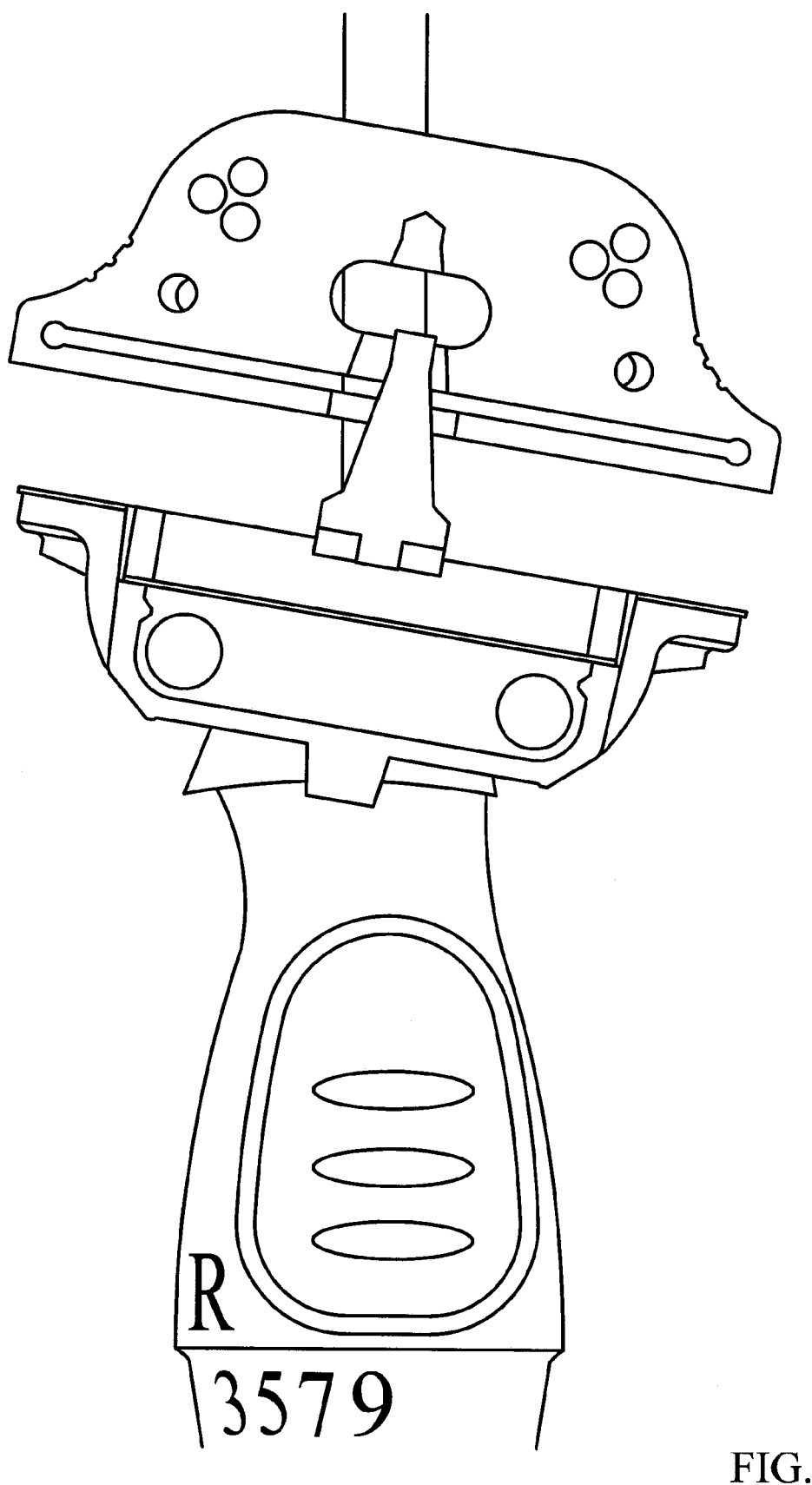
Figure 5E:
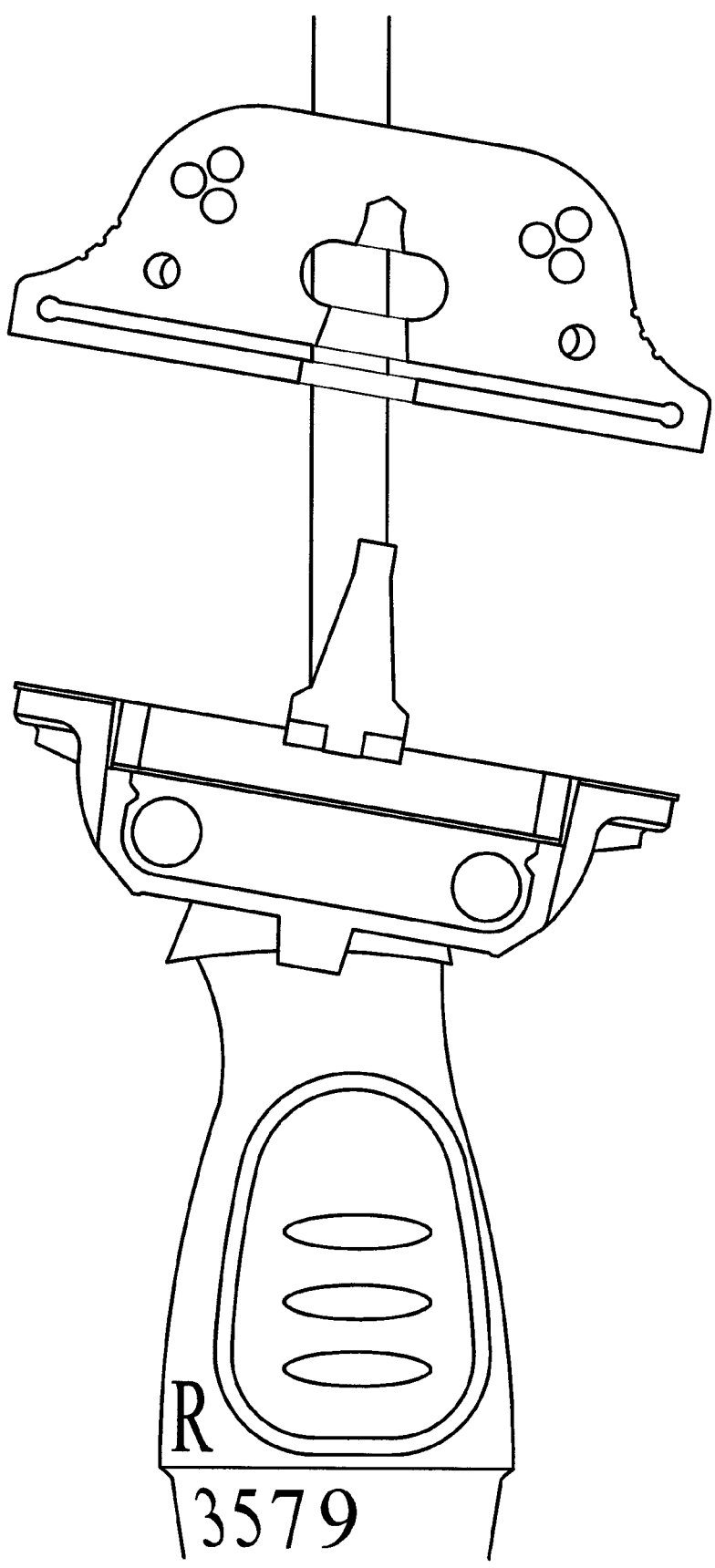

As shown in FIG. 5b, in the present system, after relatively little movement, for example as small as 1.5 mm, the first and second cylindrical sections of the connection are disengaged. After a further short movement, the first cylindrical section of the attachment protrusion enters the enlarged section 32 of the recess in the cutting guide. At this point, there is significant freedom of movement between the attachment protrusion 18 of the alignment guide and the recess 14 of the cutting guide. As shown in FIG. 5d, the disconnection of the cylindrical sections enables simple removal of the attachment protrusion along the anatomical axis defined by cylindrical section 2, without needing complicated manipulation, until as shown in FIG. 5e the attachment protrusion 18 is well clear of the cutting guide. The cylindrical section of the rod can then be withdrawn from the intramedullary canal, leaving the cutting guide in place.

Unlike prior art systems, the stepped nature of the attachment protrusion 18 and corresponding recess, including first and second cylindrical portions with different diameters, enables disconnection of an attachment protrusion to be achieved over much shorter distances. This gives greater freedom of movement between the parts, simplifying separation of the alignment guide from the cutting guide after the cutting guide is in place. This can allow a user more freedom in choice of the technique used to disconnect the cutting guide and allow one handed removal in certain circumstances.

Figure 6:
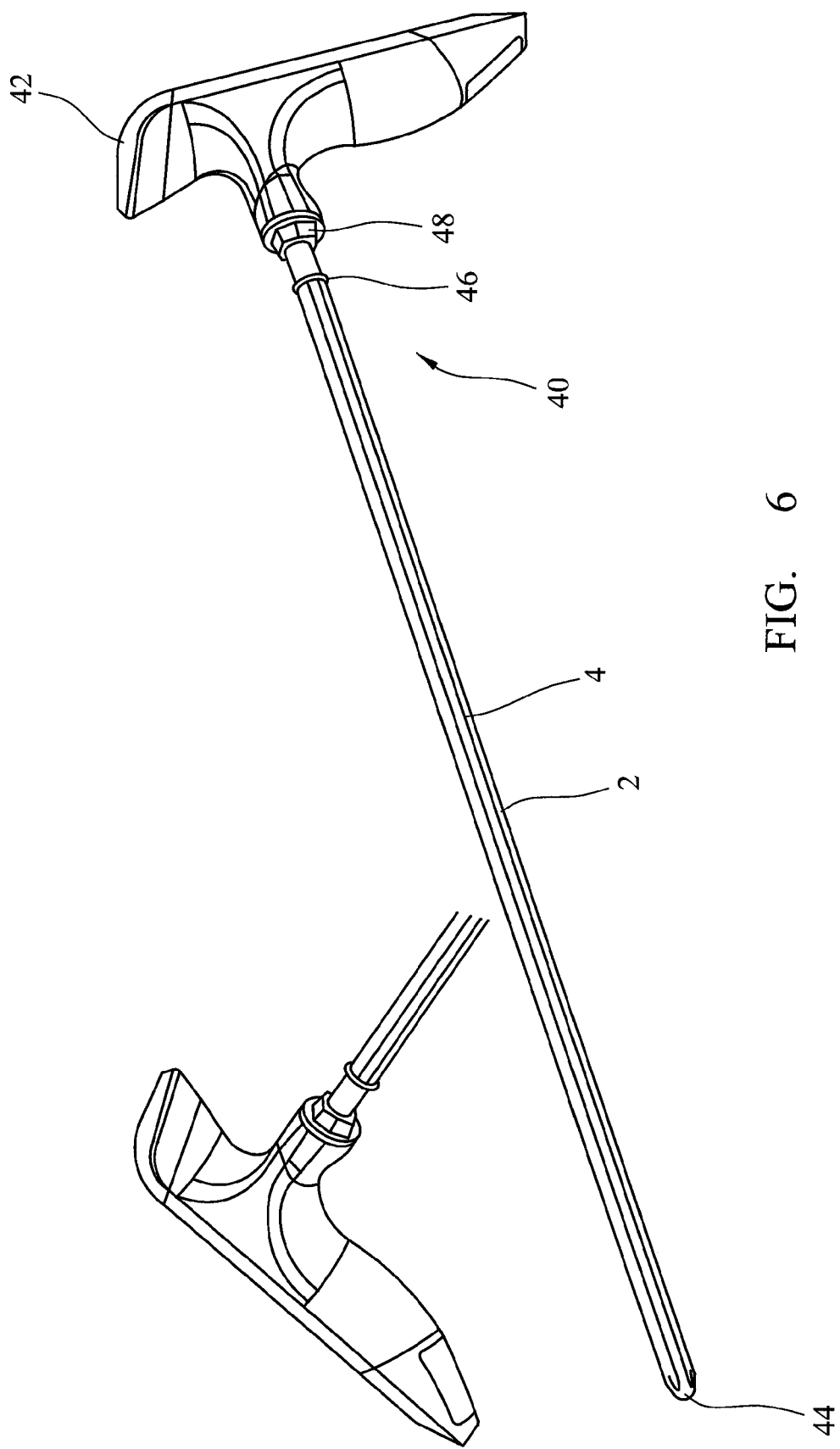
FIG. 6 depicts an intramedullary rod for use with the cutting guide and alignment guide of the system.

The system is used with an intramedullary rod 40 which is illustrated in its entirety in FIG. 6. The intramedullary rod 40 comprises a handle 42, a cylindrical section 2 having grooves 4 formed therein (as described above) and a rounded end 44 at the distal end of the cylindrical section 2, furthest from the handle 42. At a proximal end of the cylindrical section 2, close to the handle 42, a protrusion 46 is provided which extends circumferentially around the cylindrical section 2. Proximal of the protrusion 46, a second protrusion 48 is formed around the longitudinal axis defined by the cylindrical section 2. As will be described in more detail below, protrusion 46 and protrusion 48 form parts of a restraining system for retaining an alignment guide in position on the intramedullary rod 40 while the rod 40 is being inserted or removed from an intramedullary canal.

The protrusion is 46 is about 65 mm from the proximal end of the handle 42. This distance, and the length of the rod 40, may be varied depending on the length of rod 40 required to extend beyond an alignment guide 6 when engaged with the restraining system. For example, the rod 40 may extend up to 300 mm. In use the rod 40 may not be inserted into an intramedullary canal to its full length. The depth of insertion may be limited, for example by a hip stem already present in the canal from an earlier hip replacement procedure. To allow for this, the alignment guide 6 can be released from the restraining system and moved along the rod 42 to engage the bone surface.

Figure 7:
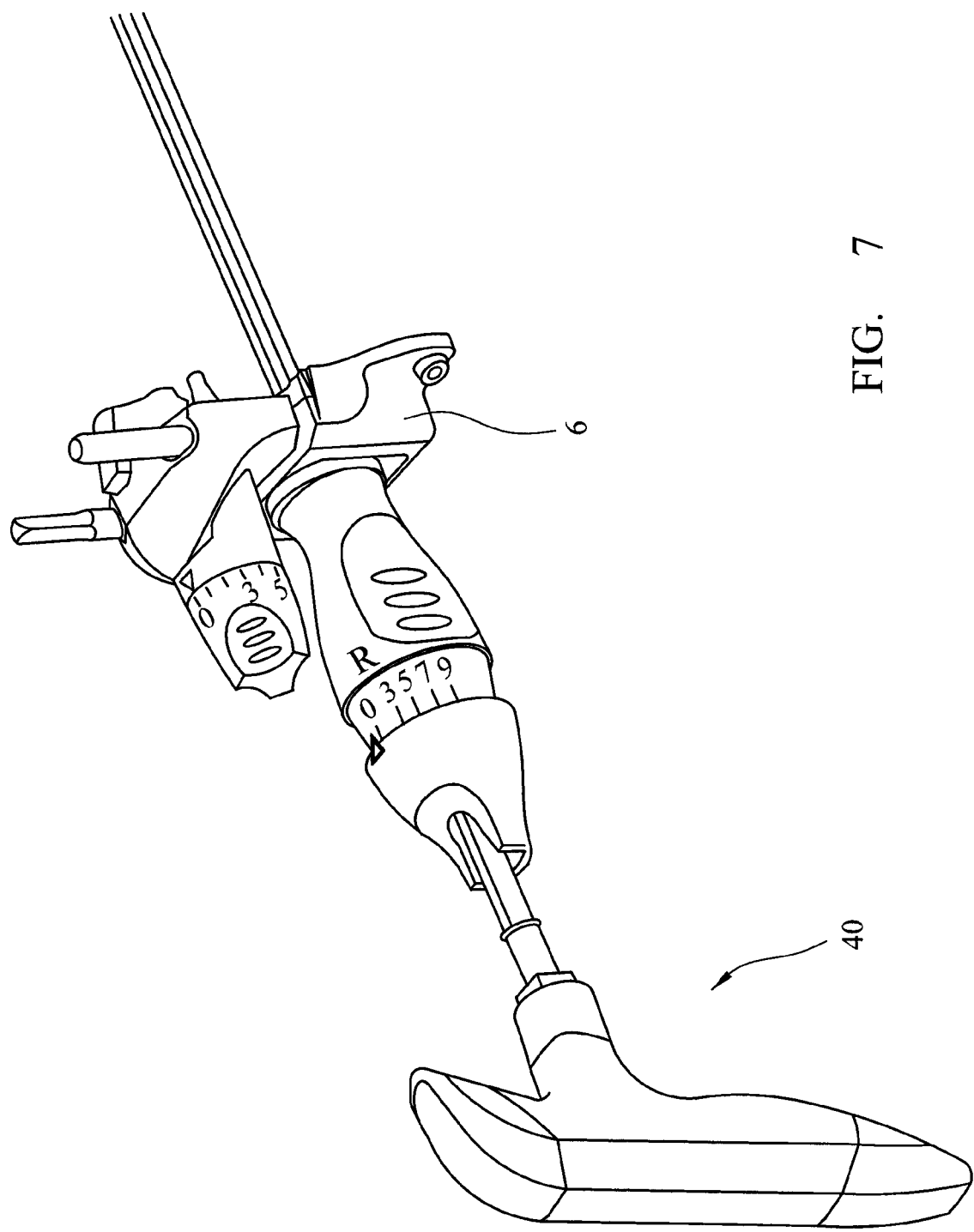
FIG. 7 depicts a perspective view of an alignment guide installed on the intramedullary rod of FIG. 6.
Figure 8:
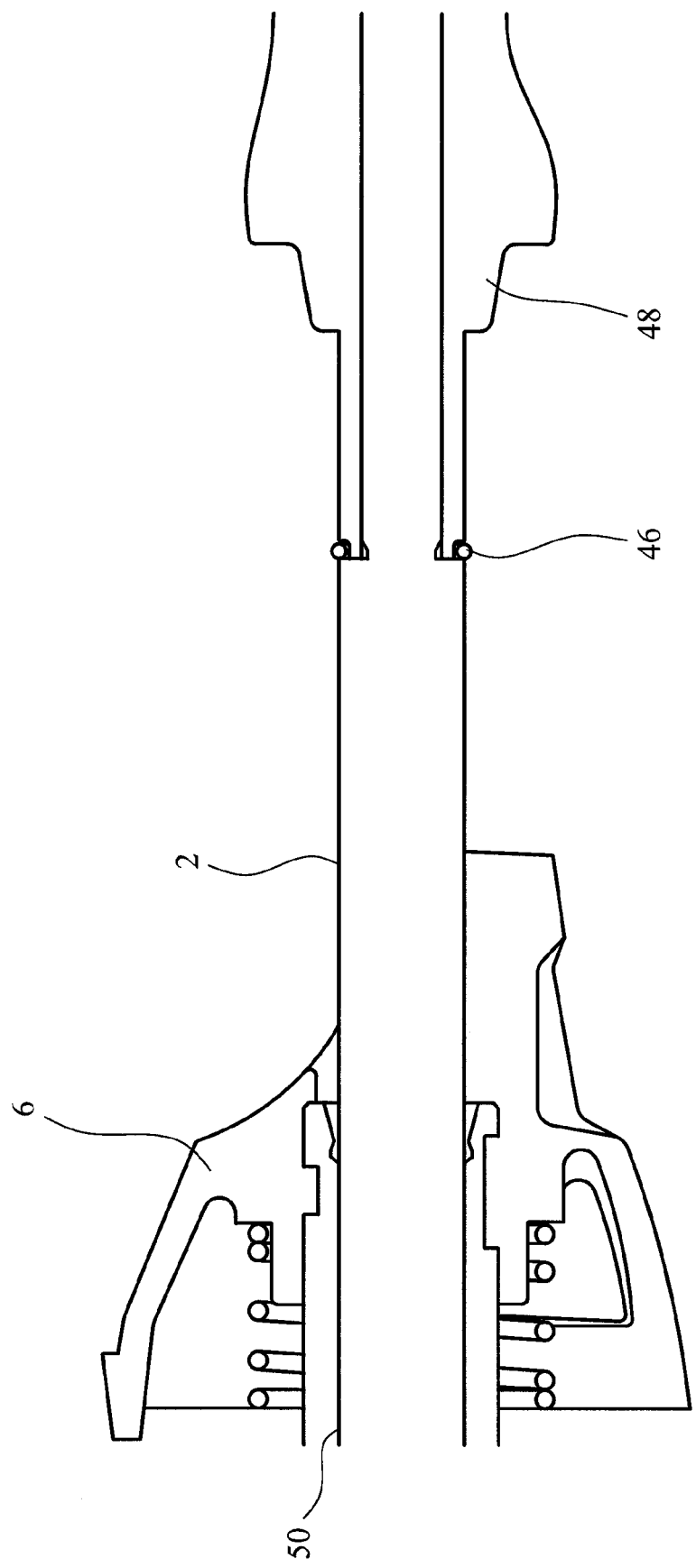
FIG. 8 depicts a cross-section through the intramedullary rod and alignment guide before the alignment guide is secured on the intramedullary rod.

FIG. 7 depicts a perspective view of the proximal end of an intramedullary rod 40 with an alignment guide 6 mounted thereon. A cross-section showing the way in which the alignment guide 6 is mounted on the intramedullary rod 40 is given in FIG. 8. FIG. 8 depicts how the alignment guide 6 comprises a through bore 50 which receives cylindrical section 2 of the intramedullary rod 40. As depicted in FIG. 8, the alignment guide 6 can be moved freely along the longitudinal axis relative to the rod and rotated relative to that axis. During insertion and removal of the intramedullary rod to the intramedullary canal, the free movement of the alignment guide can mean that two hands are required, one to insert the rod and the other to ensure that the alignment guide does not move relative to the rod during insertion.

Figure 9:
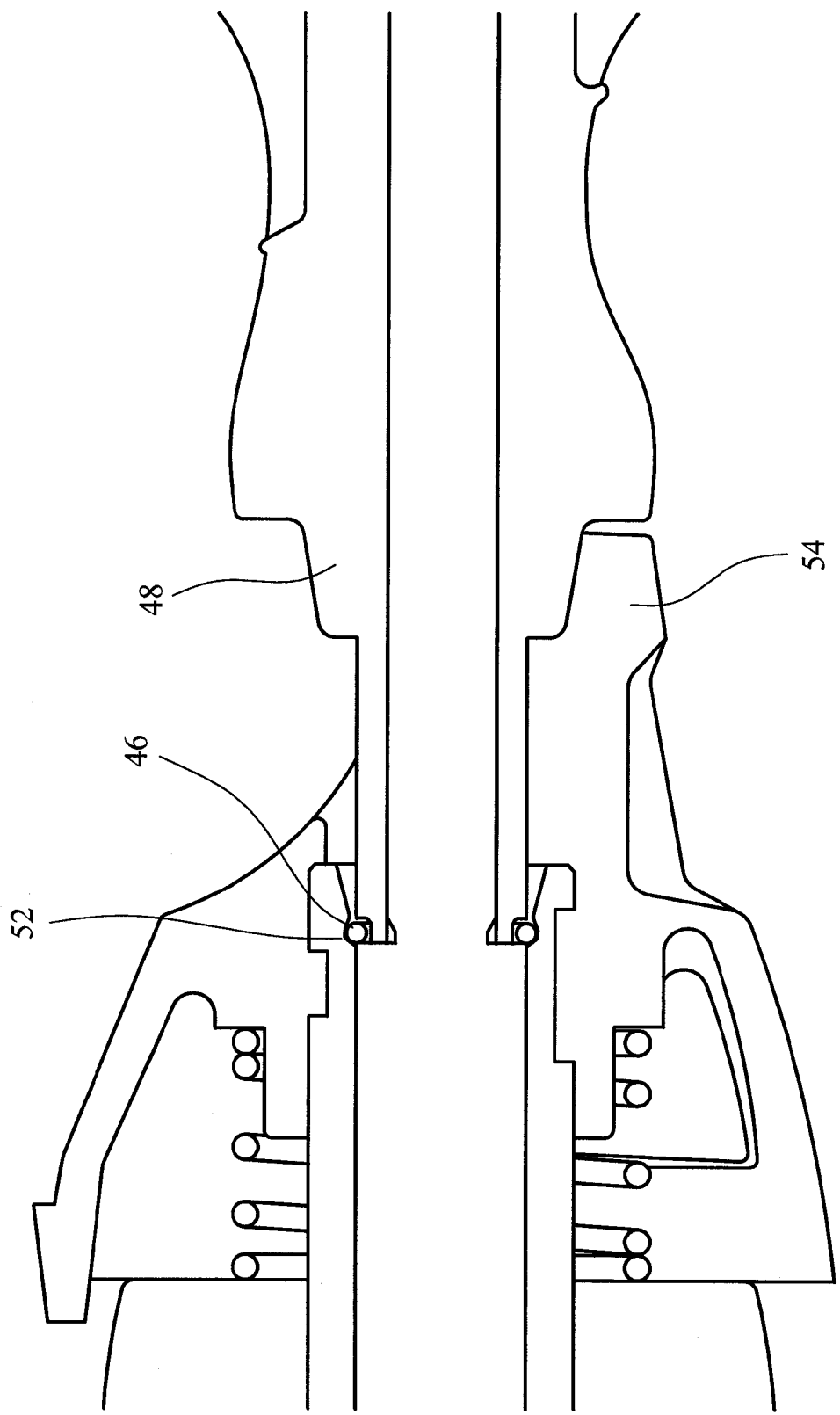
FIG. 9 depicts a cross-section through the intramedullary rod and alignment guide after the alignment guide is secured on the intramedullary rod.

To secure the alignment guide relative to the rod, FIG. 9 shows how protrusions 46, 48 engage corresponding features in the alignment guide to prevent longitudinal movement of the alignment guide along the rod and also to prevent rotation of the alignment guide relative to the rod. Ring shaped protrusion 46 on the intramedullary rod is formed from a resilient material. This engages a corresponding groove 52 in the through bore 50 of the alignment guide 6. The resilient nature of the protrusion 46 means that it can be compressed by a small force before expanding into the groove 52. This holds the alignment guide 6 securely on the rod 40, preventing relative longitudinal movement.

Figure 10:
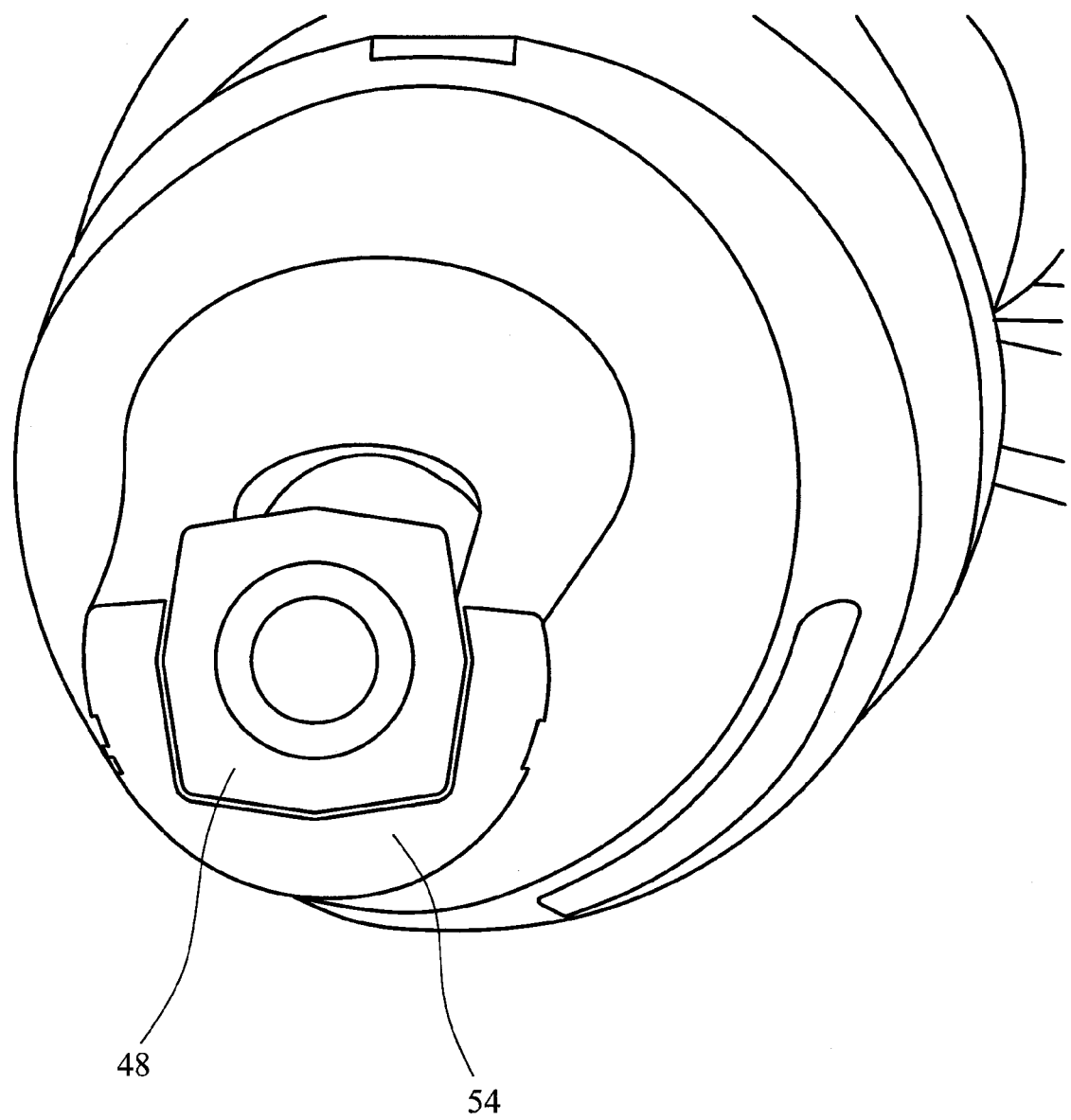
FIG. 10 depicts a cross-section showing a rotation limiting connection between the alignment guide and the intramedullary rod.

In some embodiments, the protrusion 46 may be made of a material with a high coefficient of friction so that it can also prevent rotation of the alignment guide about the longitudinal axis as well as longitudinal movement. However, a second protrusion 48 may also be provided to prevent rotation. Although not clear from the cross-section in FIG. 9, protrusion 48 has a polygonal shape centred on the longitudinal axis. This engages a corresponding recess 54 formed in the alignment guide. FIG. 10 shows the engagement between protrusion 48 and recess 54 more clearly. Protrusion 48 has a generally octagonal shape centred on the longitudinal axis. Together, the engagement of protrusion 48 with the recess 54 prevents rotation of the alignment guide 6 relative to the rod 40 when the first protrusion 48 is engaged with groove 52.

Thus, the connection between the rod and the alignment guide can be made secure during insertion or removal of the intramedullary rod. When it is desired to use the alignment guide 6 to place the cutting guide 8 in the correct position, the alignment guide 6 is moved longitudinally in a distal direction to disengage both protrusion 48 from channel 54 and protrusion 46 from groove 52. Alignment guide 6 is then free to translate and rotate about longitudinal axis of the cylindrical section 2.

Figure 11:
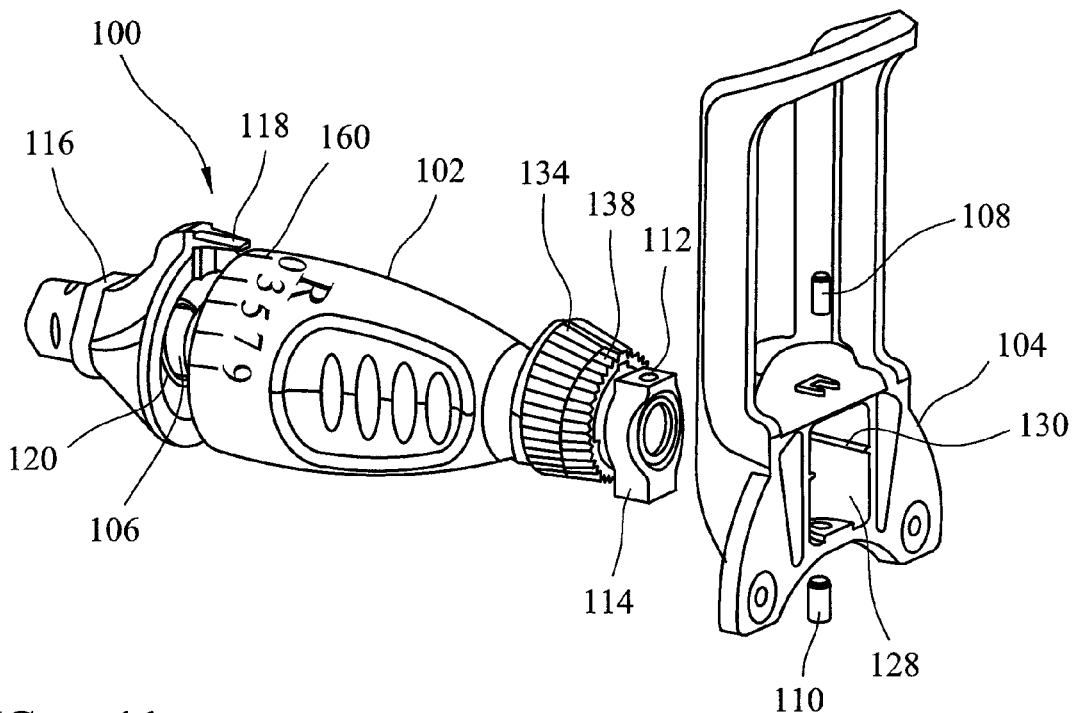
FIG. 11 depicts a perspective view of an alternative alignment guide.

FIG. 11 depicts a perspective view of an alignment guide 100 which allows a fine degree of control over the angular adjustment. As shown in FIG. 11, the alignment guide comprises an adjustment member 102 and a pivoting member 104. The adjustment member is disposed over a longitudinal shaft 106 which defines a longitudinal axis. Longitudinal shaft 106 is hollow, enabling the alignment guide to be installed on an intramedullary rod (not shown). The pivot member 104 is pivotally attached to the shaft 106 by passing pins 108, 110 through openings defined in the pivot member 104 and engaging corresponding openings 112, 114 formed in an end of the shaft 106.

An indicator member 116 is provided at the other end of the shaft to the pivotal connection. This includes a pointer 118 which extends over the end of the adjustment member 102 to overlap a visual indicia of the degree of angular adjustment applied by the adjustment member 102.

The adjustment member 102 is shorter than the distance between the end of indicator member 116 and the pivot point 112, 114. This enables adjustment member 102 to translate back and forth along the longitudinal axis 122. A resilient member 120, which is a helical spring in this embodiment, is disposed around the shaft 106. This provides a force to push the adjustment member 102 towards the pivot point 112, 114 in the absence of an applied force.

Figure 12:
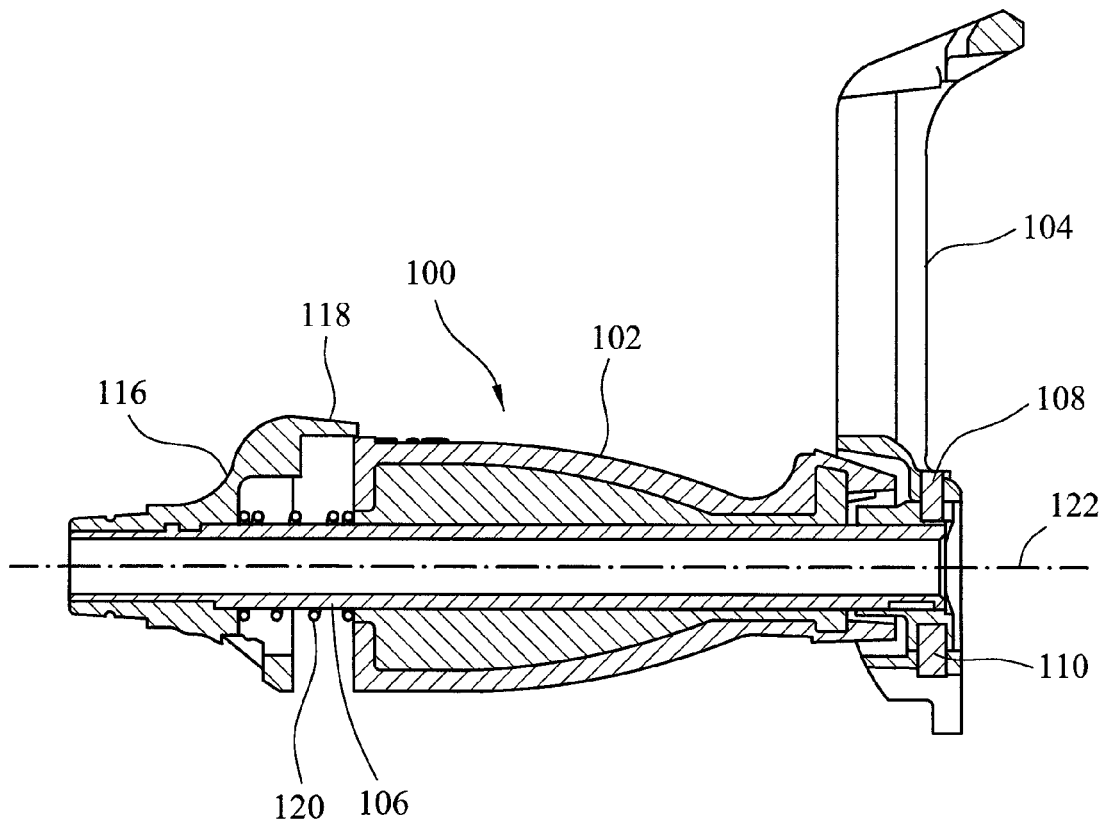
FIG. 12 depicts a cross section of the alignment guide of FIG. 11.
Figure 13:
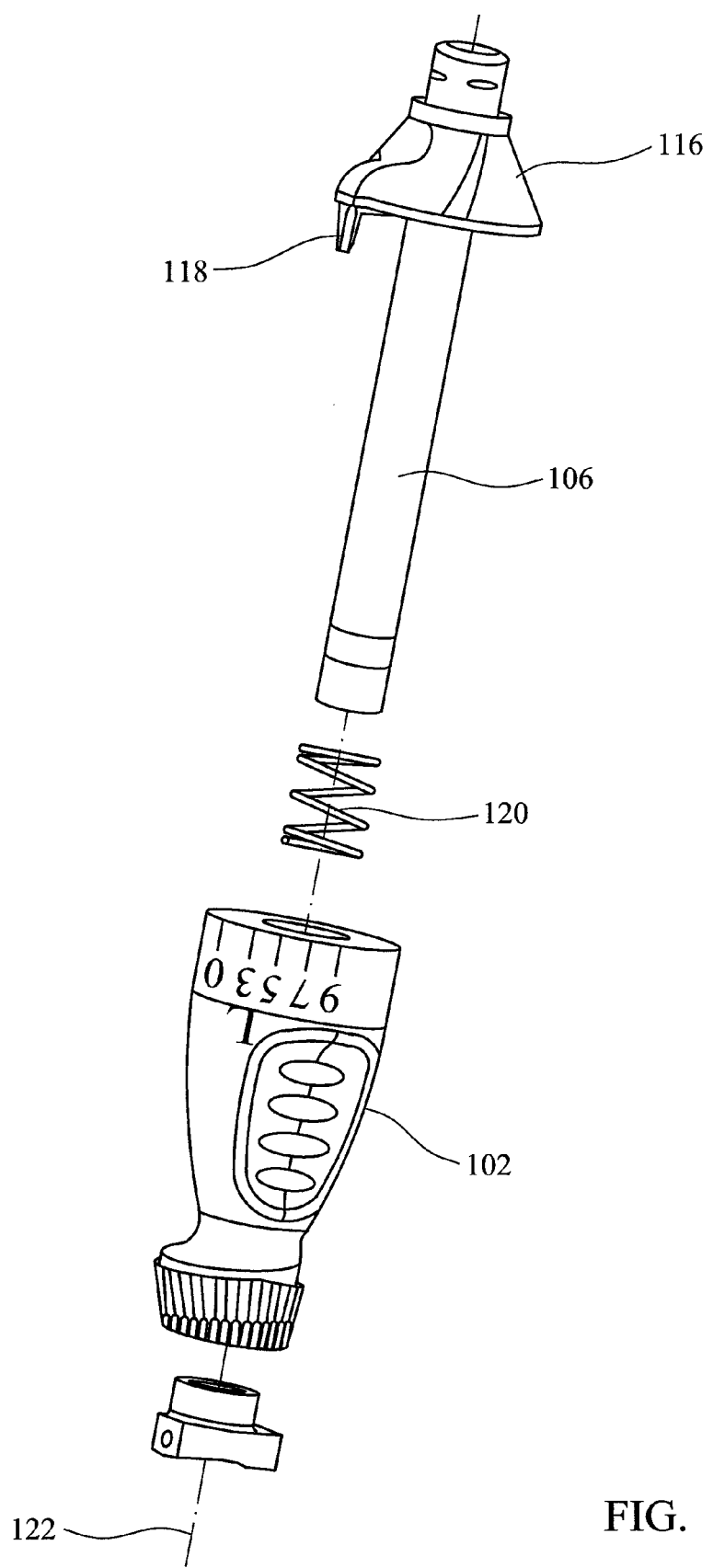
FIG. 13 depicts an exploded view of selected components of the alignment guide of FIG. 11.

The assembled alignment guide 100 is shown in cross-section in FIG. 12. This enables the relationship of the various components to the longitudinal axis 122 to be seen clearly. FIG. 13 depicts an exploded diagram showing the construction between the shaft 106, resilient member 120 and adjustment member 102.

Adjustment member 102 includes an end portion which comprises a plurality of pairs of facets 134. Each pair of facets 134 is contiguous with another pair of facets 134. The forward end of the edge between each pair of facets comprises a cut away portion 138. The configuration of the facets 134 and cut away portions 138 will be described in more detail below.

Figure 17:
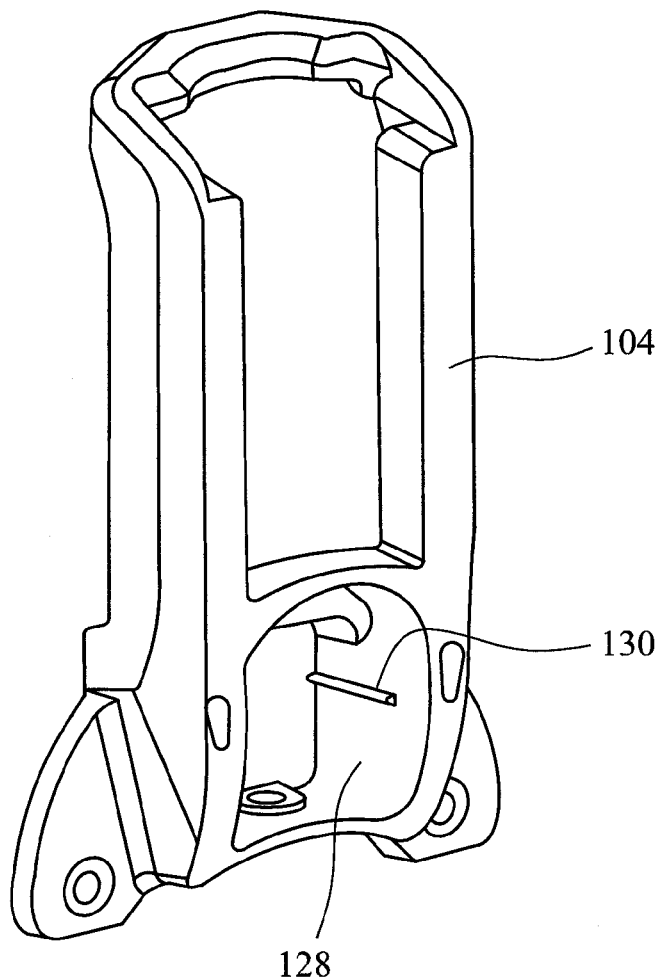
FIG. 17 depicts a perspective view of a pivoting member of the alignment guide of FIG. 13.

The pivoting member 104 comprises a recess 128 for receiving the end portion of the adjustment member. The recess 128 includes projections 130. The projections 130 are positioned to engage one pair of facets 134 when the end portion of the adjustment member 102 is located in the recess. In the absence of an applied force, the force provided by resilient member 120 ensures that a pair of facets 134 is engaged with the projections 130 of the recess 128. The configuration of the recess 128 and projections 130 can be seen more clearly in FIG. 17 which is a perspective view of the pivoting member from the opposite direction to that shown in FIG. 11.

In use, the interaction between a pair of facets 134 on the adjustment member 102 with the projections 130 on the recess 128 acts to rotate the pivoting member about the axis defined by the pins 108, 110. This pivoting is achieved by the specific arrangement of facets 134 provided on the adjustment member 102. The arrangement of these facets will now be described with reference to FIGS. 14, 15 and 16A-16C.

Figure 14:
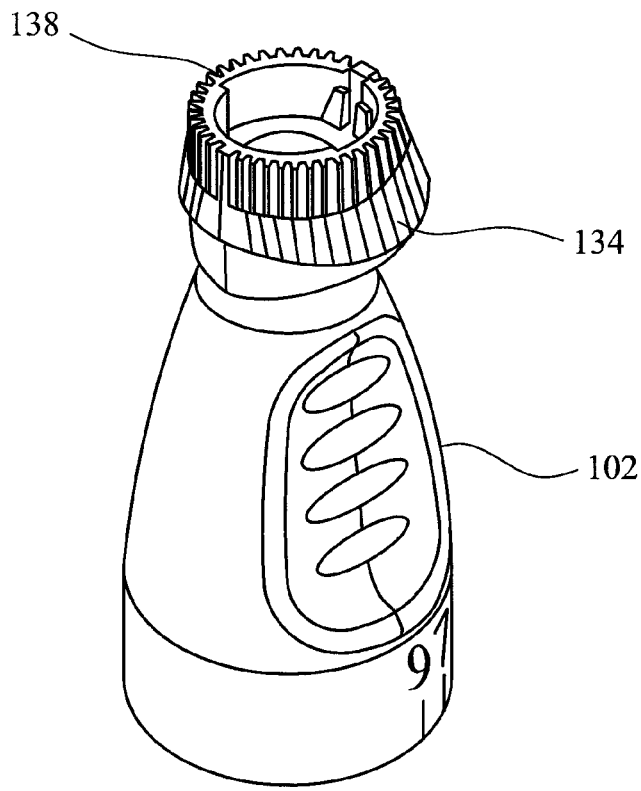
FIG. 14 depicts a perspective view of an adjustment member of the alignment guide of FIG. 13.
Figure 15:
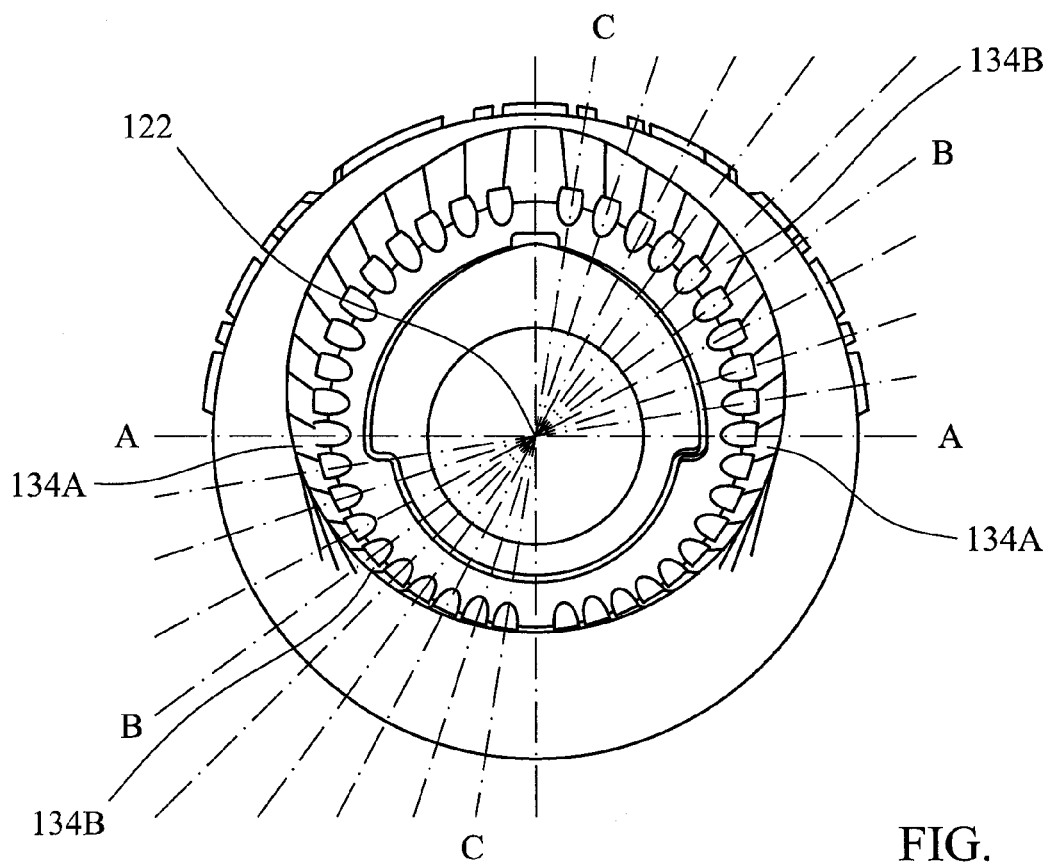
FIG. 15 depicts an end view of the adjustment member of FIG. 14.

FIG. 14 depicts a perspective view of the adjustment member 102. It shows how the adjustment member comprises a plurality of facets 134 at one end. Facets 134 are arranged in mutually opposed pairs about the longitudinal axis. The configuration of each pair of facets 134 is chosen so that they define an axis which is angled with respect to the longitudinal axis. FIG. 15 depicts an end view of the adjustment member 102. It shows how the facets are evenly spaced at regular angular spacings around the longitudinal axis 122. In this embodiment, there are nineteen pairs of facets respectively defining angles of of 0° and ±9°.

Figure 16A:
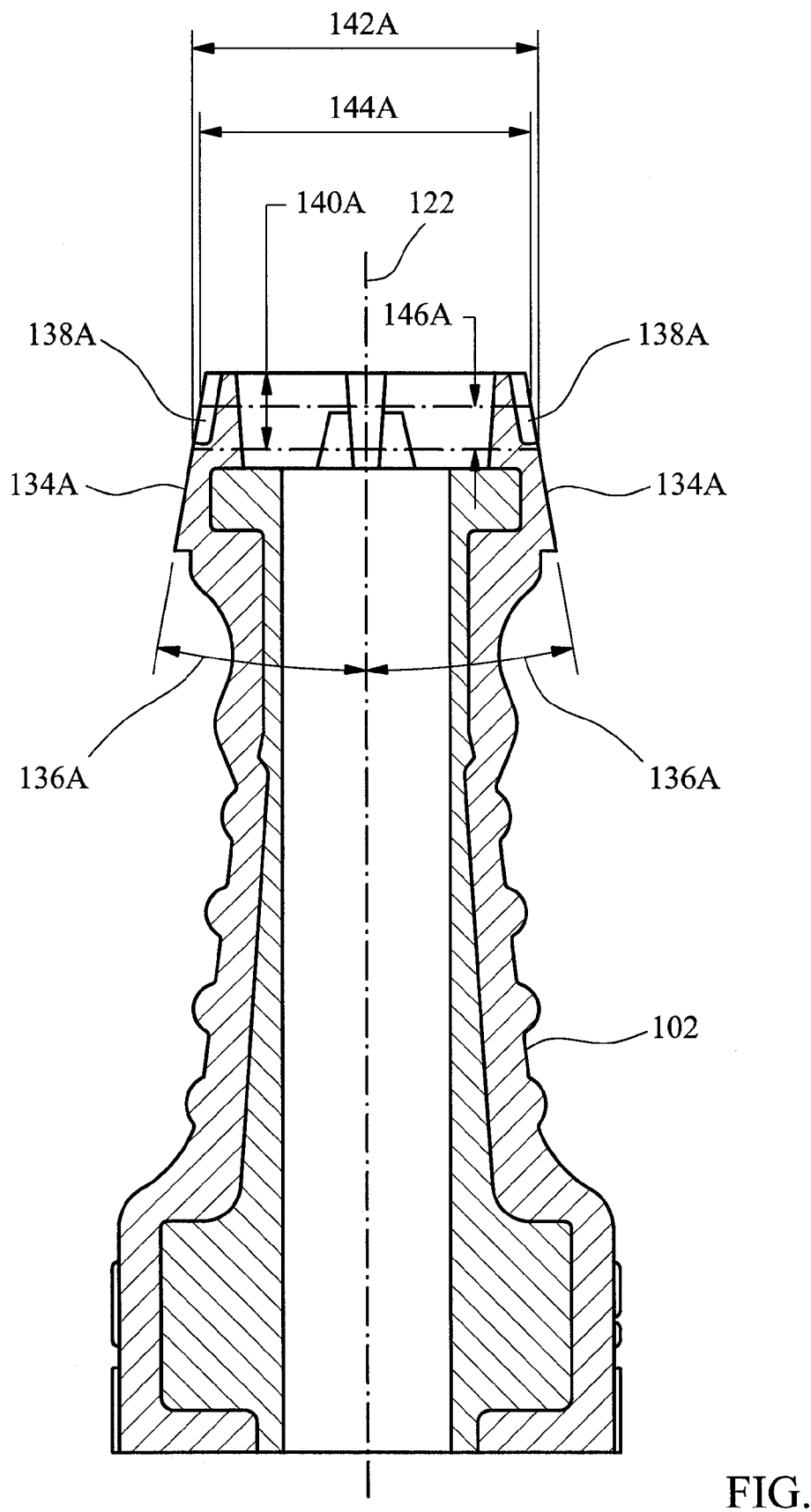
FIGS. 16A-16C depict cross sections through the adjustment member of FIG. 14.

FIG. 16A shows a cross-section along line A-A in FIG. 15. This pair of facets 134A defines an axis which is coincident with the longitudinal axis 122, or at an angle of 0°. In this example, all of the pairs of facets 134 define a taper of 20°. Thus, both facets 134A are offset by 10° from the longitudinal axis to define a taper of 20°. This angular adjustment is indicated by arrows 136A in FIG. 16A.

As discussed above, to facilitate rotation of the adjustment member 102 when it is disengaged from the recess, cut outs 138 are provided at the end. Cut outs 138A depicted in FIG. 16A extend approximately 5.5 mm from the end of the adjustment member 102. This is indicated by reference numeral 140A. The width of the adjustment member just before the cut out is approximately 25 mm, indicated by reference number 142A. Dimension 144A is approximately 24 mm, showing the taper and dimension 136A is approximately 3 mm. Other dimensions may be used in other embodiments depending on the particular requirements.

For an angle of 0°, i.e. an axis which is coincident with the longitudinal axis FIG. 16A shows that the configuration of the end portion in cross-section at the pair of facets 134A is symmetrical. Thus, when pair of facets 134A engage the projections 130 the recess is rotated to be aligned with the longitudinal axis.

Figure 16B:
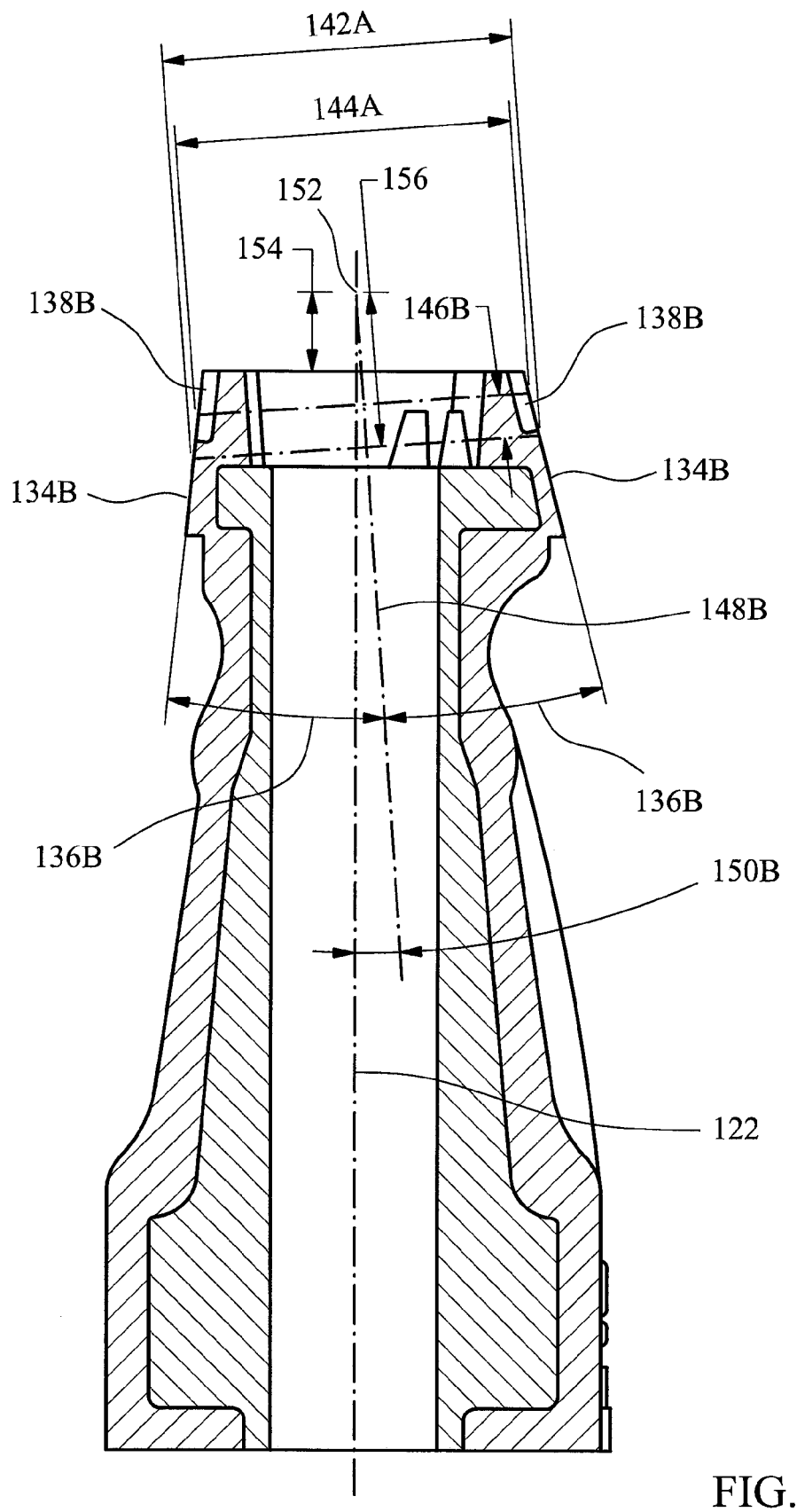

FIG. 16B depicts a cross-section along line B-B in FIG. 15. At this position, the pair of facets 134B together define an angled axis 148B with respect to the longitudinal axis 122. As indicated by angular dimension 150B, the angled axis 148B is 4° offset from longitudinal axis 122. Angled axis 148B is defined by facets 134B which have been rotated about a point 152. Point 152 lies on the longitudinal axis 122 approximately 5.5 mm from the top of the adjustment member 102, as indicated by distance 154. The taper of the facets 134B is the same as for facets 134A, 20°. However, the taper is defined with reference to the angled axis 148B. This means that when the facets 134B engage the projections 130 the pivoting member will be pivoted through 4° because of the self-centering nature of the taper. Point 152 is chosen to be coincident with the axis of pins 108, 110.

When facets 134B are engaged with pivoting member, the pivoting member is rotated relative to the longitudinal axis consistent with the rotation of the facets 134B along angled axis 148B. Thus, the cut out 138B extends a different distance either side of the adjustment member 102 to ensure that they are the same distance from the pivot member, when facets 134B are engaged by projections 130. Dimension 156 is approximately 11 mm from the pivot point 152. This 11 mm distance is measured in the direction of angled axis 148B. Thus, cut out 138B is shorter than cut out 138B'. Dimensions 142B, 144B and 146B correspond to dimensions 142A, 144A and 146A for consistency with all embodiments.

Figure 16C:
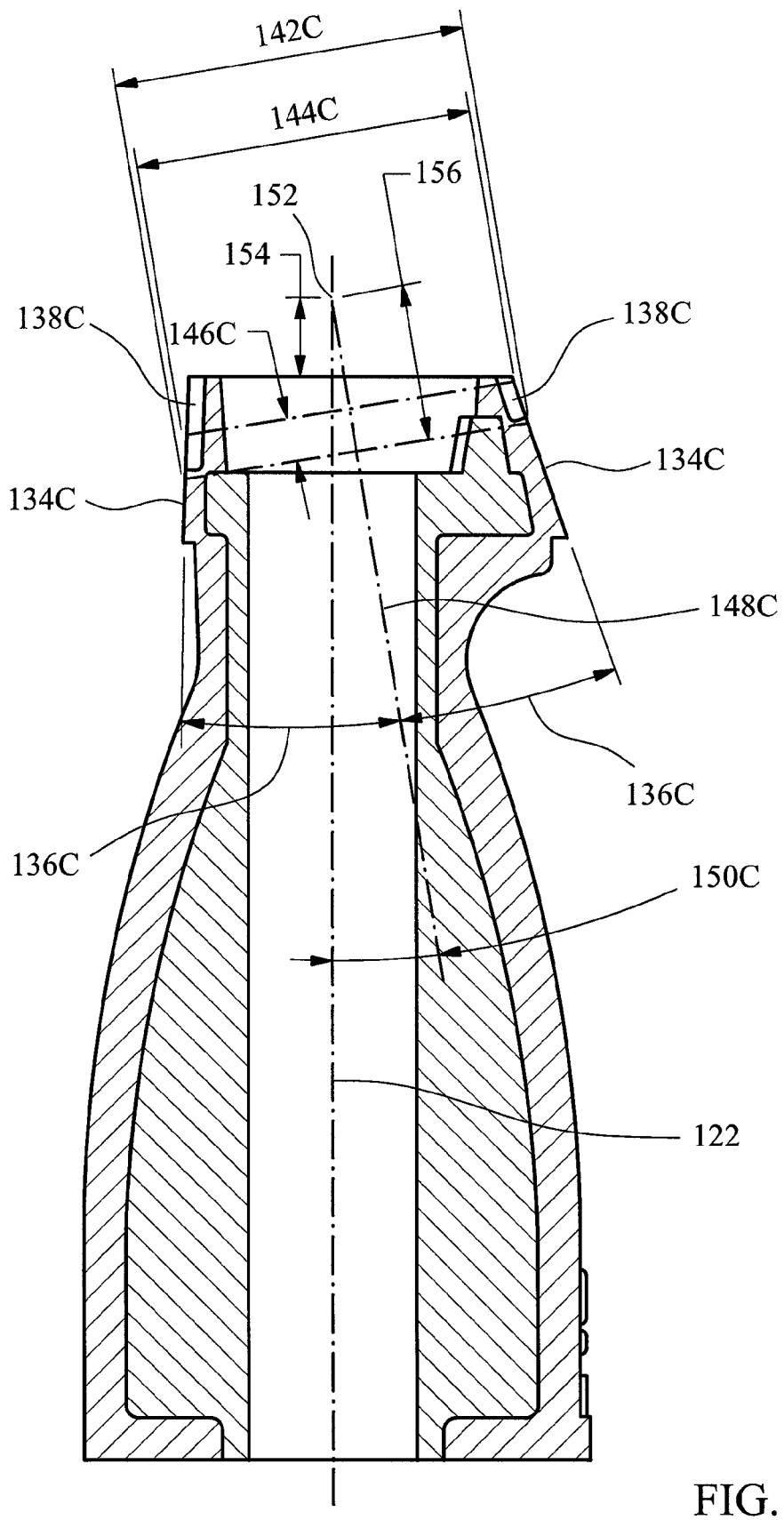

To further assist the explanation, FIG. 16C depicts a cross-section of the adjustment member 102 taken along line CC in FIG. 15. This corresponds to an adjustment of 9° as indicated by angle 150C in FIG. 16C. The angling of angled axis 148C is more pronounced in this cross-section. This means that the distance of cut outs 138C on the right hand side of the diagram is again shorter than the cut out 138C' on the left hand side. The length of the cut out is again determined by projecting a line approximately 11 mm from the pivot point 152 and extending the cutout 138C, 138C' in the direction of the angled axis 148C distance 156 (approximately 11 mm in this embodiment). The remaining dimensions 142C, 144C, 146C remain the same as 142A, 144B and 146C.

FIG. 16C demonstrates how the facets 134C are still tapered with respect to the longitudinal axis 122. This is because the taper angle of 20° means that with the 9° relative angle of axis 148C there remains 1° of taper depicted on the left hand side of FIG. 16C. This ensures that the taper remains with respect to the longitudinal axis (although it is not symmetrical about the longitudinal axis 122).

In use, the angle of the pivoting member is adjusted by withdrawing the adjustment member 102 proximally against the biasing force of resilient member 120. This disengages the facets from the projections in the pivoting member 104. The adjustment member is then rotated until the indicator 118 points at the desired degree of angular adjustment. This is indicated by markings or indicia 160 on the adjustment member 102. The adjustment member can then be released and the action of the resilient member 120 pushes the end of the adjustment member into the recess 128 of the pivoting member. The pair of facets 134 corresponding to the desired angular adjustment as indicated by indicator 118 engage projections 130. The taper ensures that the pivoting member is centred and securely located on the facets. Depending on the angle of the axis defined by the pair of facets, the pivoting member is turned to the desired angle by the engagement of the facets with the projection.

Figure 18:
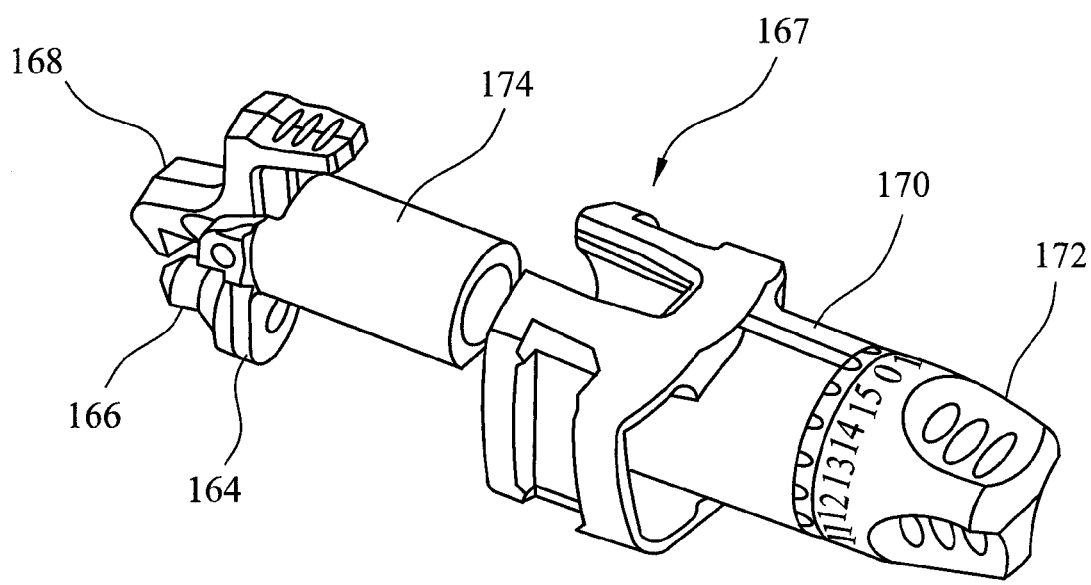
FIG. 18 depicts an exploded view of a cutting guide attachment part for use with the alignment guide of FIG. 16.

In this embodiment, a cutting guide is attached to the pivoting member 104 by an intermediate translating assembly 162. Translating assembly 162 comprises an attachment member 164 which includes a stepped connection 166 and clip 168 for attaching a cutting guide (not shown) and a translation adjustment mechanism 170. Translation adjustment mechanism 170 comprises an adjustment dial 172 which adjusts the translation of the cutting guide relative to the alignment guide by adjusting the degree to which shaft 174 is inserted into a corresponding recess in translation adjustment guide 170. (The parts of this assembly are shown in exploded form in FIG. 18 for clarity).

It will be appreciated that the configuration depicted in FIGS. 11-18 differs in some minor aspects of appearance with configuration depicted in FIGS. 1-10 and 19. The features of angular adjustment and features of the adjustment member described in relation to FIGS. 11-18 can be applied to FIGS. 1-10 and 19.

Where dimensions are described, they are for example only and are not limiting. Alternative dimensions may be used in other embodiments.

Figure 19:
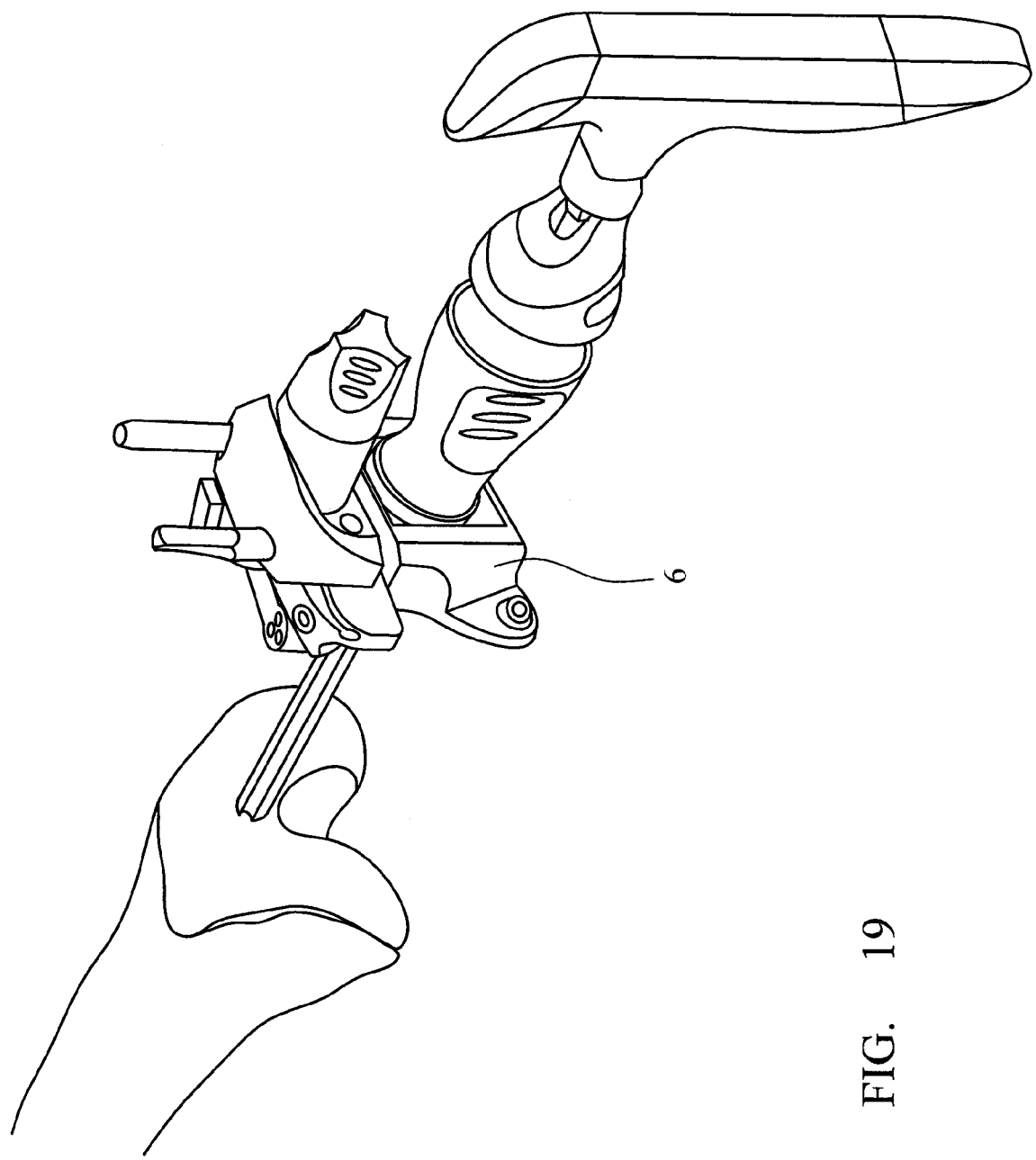
FIG. 19 depicts a perspective view of an alignment guide, cutting guide and intramedullary rod with the intramedullary rod inserted to the intramedullary canal of a femur.

FIG. 19 depicts a system of alignment guide, rod, handle and cutting guide in use, inserted into a femur before the alignment guide is advanced along the rod to engage the cutting guide with the femur.

The improved connection between a cutting guide and an alignment guide may be used in other applications than for knee surgery, for example, it is applicable to any situation in which an alignment axis is not the same as a guiding axis. The stepped principle could also be applied to any system in which disconnection with short longitudinal movement is required. The connection between the alignment guide and the rod may be used in any circumstance in which an alignment guide is used with a rod, not only those where an alignment guide is used to install a cutting guide for knee surgery as described above. The improved angular adjustment mechanism may be used with any surgical instrument requiring angular adjustment, not only for use in knee surgery.

Although a system comprising an alignment guide, cutting guide and rod has been described, the stepped attachment protrusion for connecting the cutting guide and alignment guide can be used in systems which do not include a rod. Likewise the restraining system between the alignment guide and rod can be used in systems which do not include a cutting guide. The stepped attachment system and the restraining system can be used with other alignment guides than the faceted guide described above, for example they may be used with the mechanism discussed in WO-A-2009/037471.

The elements of the above described system are constructed from medical grade materials. For example the rod may be manufactured from medical grade metal and the other components from medical grade plastics materials or metals.

The invention claimed is:

1. A surgical instrument assembly comprising:
an adjustment member comprising a plurality of pairs of facets arranged about a longitudinal axis, each pair of facets meeting along an edge, the adjustment member being rotatable about the longitudinal axis; wherein each edge of the plurality of pairs of facets lies along a line intersecting the longitudinal axis at an angle, each edge defining a different angle with respect to the longitudinal axis;
a pivoting member pivotable about a pivot axis that is perpendicular to the longitudinal axis, the pivoting member having a recess sized to engage at least one pair of the plurality of pairs of facets; and
a cutting guide attached to the pivot member.

2. The surgical instrument assembly of claim 1, further comprising a intramedullary rod defining an intramedullary axis, and wherein the angular adjustment mechanism is connected to the intramedullary rod, and the longitudinal axis of the adjustment member is coaxial with the intramedullary axis.

* * * * *